(12) United States Patent
Sosalla et al.

(10) Patent No.: US 7,956,234 B2
(45) Date of Patent: Jun. 7, 2011

(54) DISPOSABLE GARMENT HAVING IMPROVED GRAPHICS

(75) Inventors: Paula M. Sosalla, Appleton, WI (US); Theodore T. Tower, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1580 days.

(21) Appl. No.: 11/025,528

(22) Filed: Dec. 29, 2004

(65) Prior Publication Data

US 2005/0143698 A1  Jun. 30, 2005

Related U.S. Application Data

(60) Provisional application No. 60/533,673, filed on Dec. 31, 2003.

(51) Int. Cl.
*A61F 13/15* (2006.01)
*G01N 31/00* (2006.01)

(52) U.S. Cl. .................. 604/361; 604/364; 604/385.01; 252/408.1

(58) Field of Classification Search .................. 604/361, 604/364, 385.01; 252/408; 128/886; 116/206
See application file for complete search history.

(56) References Cited

U.S. PATENT DOCUMENTS

| 4,704,116 | A |   | 11/1987 | Enloe |
| 6,075,178 | A | * | 6/2000 | La Wilhelm et al. ......... 604/361 |
| 6,181,816 | B1 | * | 1/2001 | Adams et al. ................. 382/162 |
| 6,297,424 | B1 | * | 10/2001 | Olson et al. .................... 604/361 |
| 2003/0044578 | A1 |   | 3/2003 | Nissing |
| 2003/0073966 | A1 |   | 4/2003 | Sosalla et al. |

FOREIGN PATENT DOCUMENTS

| EP | 1 147 755 A2 | 10/2001 |
| WO | WO 00/76439 A2 | 12/2000 |
| WO | WO 03/053313 A2 | 7/2003 |

OTHER PUBLICATIONS

Marziliano, Pina et al., "Perceptual Blur and Ringing Metrics: Application to JPEG2000," *Signal Processing: Image Communication*, 19 (2004), Elsevier Science, 2003, pp. 163-172.

* cited by examiner

*Primary Examiner* — Jacqueline F. Stephens
(74) *Attorney, Agent, or Firm* — Henry M. Kubicki; David J. Arteman

(57) ABSTRACT

A disposable garment having a multicolored scene graphic is disclosed. In particular embodiments, the multicolored scene graphic includes a focal graphic and a background graphic, wherein the background graphic appears blurry relative to the focal graphic to enhance the conspicuousness of the focal graphic. Methods for making such articles are also disclosed.

3 Claims, 23 Drawing Sheets
(22 of 23 Drawing Sheet(s) Filed in Color)

| Example RGB and HSV quantities | | | | | | | |
|---|---|---|---|---|---|---|---|
| Red | Green | Blue | Color | Patch | Hue | Sat | Value |
| 1 | 1 | 1 | White | | 0 (N.A.) | 0 | 1 |
| 0 | 1 | 0 | Green | | 0.33 | 1 | 1 |
| 1 | 0 | 0 | Red | | 0 | 1 | 1 |
| 1 | 0.5 | 0.5 | Pink | | 0 | 0.5 | 1 |
| 0.5 | 0.5 | 0.5 | Gray | | 0 (N.A.) | 0 | 0.5 |
| 0 | 0 | 0 | Black | | 0 (N.A.) | 0 | 0 |

FIG. 15

| Image | ROI | MG(h) | MG(s) | MG(v) | Color Attribute | MaxMG per mm | Characteristic width [mm] |
|---|---|---|---|---|---|---|---|
| | | | | | H | 0.43 | 2.31 |
| | | | | | S | 0.87 | 1.15 |
| | | | | | V | 1.87 | 0.53 |
| | | | | | H | 0.27 | 3.69 |
| | | | | | S | 0.91 | 1.10 |
| | | | | | V | 0.56 | 1.79 |

FIG. 17

FIG. 20 6.7 Pixel Blur

| Example | Focal Graphic ROI (from Fig. 22) | Background Graphic ROI (from Fig. 18) | Background Graphic ROI (from Fig. 19) | Background Graphic ROI (from Fig. 20) | Background Graphic ROI (from Fig. 21) | Background Graphic ROI (from Fig. 22) |
|---|---|---|---|---|---|---|
| Blur | No Blur | 0 pixels (no blur) | 3.4 pixels | 6.7 pixels | 11 pixels | 25 pixels |
| Region of Interest | | | | | | |
| Hue Width (mm) | 0.24 | 0.17 | 0.28 | 0.44 | 0.82 | 1.16 |
| Sat Width (mm) | 0.31 | 0.27 | 0.49 | 0.66 | 0.82 | 1.18 |
| Val Width (mm) | 0.40 | 0.38 | 1.46 | 2.82 | 4.85 | 6.79 |
| HSV Width (mm) | 0.22 | 0.17 | 0.27 | 0.43 | 0.81 | 1.16 |

FIG. 23

DISPOSABLE GARMENT HAVING IMPROVED GRAPHICS

This application claims priority to Provisional Application Ser. No. 60/533,673 entitled Disposable Garment Having Improved Graphics and filed in the U.S. Patent and Trademark Office on Dec. 31, 2003. The entirety of Provisional Application Ser. No. 60/533,673 is hereby incorporated by reference.

BACKGROUND OF THE INVENTION

Disposable garments are common in today's society. For example, disposable training pants, disposable enuresis pants, and disposable swim garments find widespread use among both children and adults. In many instances, these disposable products are adapted to contain or absorb bodily fluids discharged by the wearer.

It is generally desirable for such garments to be visually appealing to both the wearer and to others viewing the garment, such as a caregiver. For example, parents of toilet training children frequently choose to employ disposable training pants during the toilet training process. Children generally desire that their disposable training pants resemble real underwear. Further, it has been discovered that disposable training pants having bold and engaging graphical images disposed thereon often make the disposable training pants more desirable to children. For example, a popular children's character engaged in some activity, disposed on a training pant (such as by printing), has been found to significantly increase the appeal of the training pant to children. However, conventional training pants having conventional graphics thereon have failed to adequately capture the interest of children, and thus room for improvement exists.

SUMMARY OF THE INVENTION

It has been discovered that increasing the noticeability or conspicuousness of certain portions of the graphical depictions on disposable garments further increases the appeal of disposable garments, such as for disposable training pants. For example, it can be desirable to children for a character with which they are familiar to "stand out" in a depicted scene. Prior art garments having graphics have not satisfactorily increased the noticeability or conspicuouness of desired portions of the graphics disposed within or upon the garment.

In response to the aforementioned deficiency in the art, a disposable garment having improved graphics and a method for making such garments have been invented. In general terms, the disposable garment of the present invention includes a multicolored scene graphic comprised of a focal graphic and a background graphic. The multicolored scene graphic is constructed such that the focal graphic "stands out" from the background graphic. In certain embodiments, the background graphic includes one or more blurred portions or edges intended to increase the conspicuousness of the focal graphic.

In one aspect, the present invention is directed to a disposable garment having a multicolored scene graphic. In one embodiment, the disposable garment of the present invention includes a multicolored scene graphic disposed thereon, the multicolored scene graphic comprising a focal graphic comprising at least one color transition region exhibiting a characteristic hue transition width of at most about 2.5 millimeters; and a background graphic comprising at least one color transition region exhibiting a characteristic hue transition width of at least about 0.3 millimeters.

In another embodiment, the disposable garment of the present invention includes a multicolored scene graphic disposed thereon, the multicolored scene graphic comprising a focal graphic comprising at least one color transition region exhibiting a characteristic saturation transition width of at most about 1.0 millimeters; and a background graphic comprising at least one color transition region exhibiting a characteristic saturation transition width of at least about 0.25 millimeters.

In still another embodiment, the disposable garment of the present invention includes a multicolored scene graphic disposed thereon, the multicolored scene graphic comprising a focal graphic comprising at least one color transition region exhibiting a characteristic value transition width of at most about 1.6 millimeters; and a background graphic comprising at least one color transition region exhibiting a characteristic value transition width of at least about 0.9 millimeters.

In yet another embodiment, the disposable garment of the present invention includes a multicolored scene graphic disposed thereon, the multicolored scene graphic comprising a focal graphic and a background graphic, wherein at least about 50% of an area of the background graphic exhibits a Gaussian blur effect of at least about 4 pixels.

In still another embodiment, the disposable garment of the present invention includes a multicolored scene graphic disposed thereon, the multicolored scene graphic comprising a focal graphic, wherein at least 95% of an area of the focal graphic appears substantially unblurred to person of 20/20 vision viewing the scene graphic from a distance of two feet outdoors on a clear day; a background graphic, wherein at least 95% of an area of the background graphic appears blurrier than the at least 95% substantially unblurred area of the focal graphic to a person of 20/20 vision viewing the scene graphic from a distance of two feet outdoors on a clear day.

In yet another embodiment, the disposable garment of the present invention includes a multicolored scene graphic disposed thereon, the multicolored scene graphic comprising a focal graphic comprising at least one color transition region exhibiting a characteristic hue transition width, a characteristic saturation transition width, and a characteristic value transition width; a background graphic comprising at least one color transition region exhibiting a characteristic hue transition width, a characteristic saturation transition width, and a characteristic value transition width, wherein at least about 80% of an area of the focal graphic includes no color transition regions having a characteristic hue transition width about 75% or greater than that of a characteristic hue transition width of any color transition regions within at least about 80% of an area of the background graphic, wherein at least about 80% of an area of the focal graphic includes no color transition regions having a characteristic saturation transition width about 75% or greater than that of a characteristic saturation transition width of any color transition regions within at least about 80% of an area of the background graphic, and wherein at least about 80% of an area of the focal graphic includes no color transition regions having a characteristic value transition width about 75% or greater than that of a characteristic value transition width of any color transition regions within at least about 80% of an area of the background graphic; and further wherein the focal graphic includes at least one character graphic, and wherein the multicolored scene graphic includes at least one garment-feature graphic.

In another aspect, the present invention is directed to a method for making a disposable garment having a multicolored scene graphic disposed on a substrate. In one embodiment, the method comprises providing a background graphic design; applying a Gaussian blur of at least about 4 pixels to at least about 50% of an area of the background graphic design to create a blurred background graphic design; providing a focal graphic design; and disposing the blurred background graphic design and the focal graphic design on the substrate.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 15 lists normalized RGB values and the corresponding normalized HSV values for various colors;

FIG. 17 representatively illustrates regions of interest taken from the focal graphic and background graphic portions of the multicolored scene graphic depicted in FIG. 5, selected color transition regions from the focal graphic and background graphic regions of interest, and color-attribute transition data for those color transition regions in accordance with one Example in accordance with the invention.

FIG. 23 representatively illustrates regions of interest taken from the focal graphic and background graphic portions of the multicolored scene graphics depicted in FIGS. 18-22, and average color-attribute transition data for the color transition regions within those regions of interest in accordance with another Example in accordance with the invention.

Corresponding parts are indicated by corresponding reference numbers throughout the drawings.

DETAILED DESCRIPTION OF THE INVENTION

The principles of the present invention can be incorporated into a variety of disposable garments, such as disposable absorbent garments. The term "disposable" refers to garments which are designed to be discarded after a limited use rather than being laundered or otherwise restored for reuse. For ease of explanation, the description hereafter will be in terms of a child's training pant.

Figure 1:
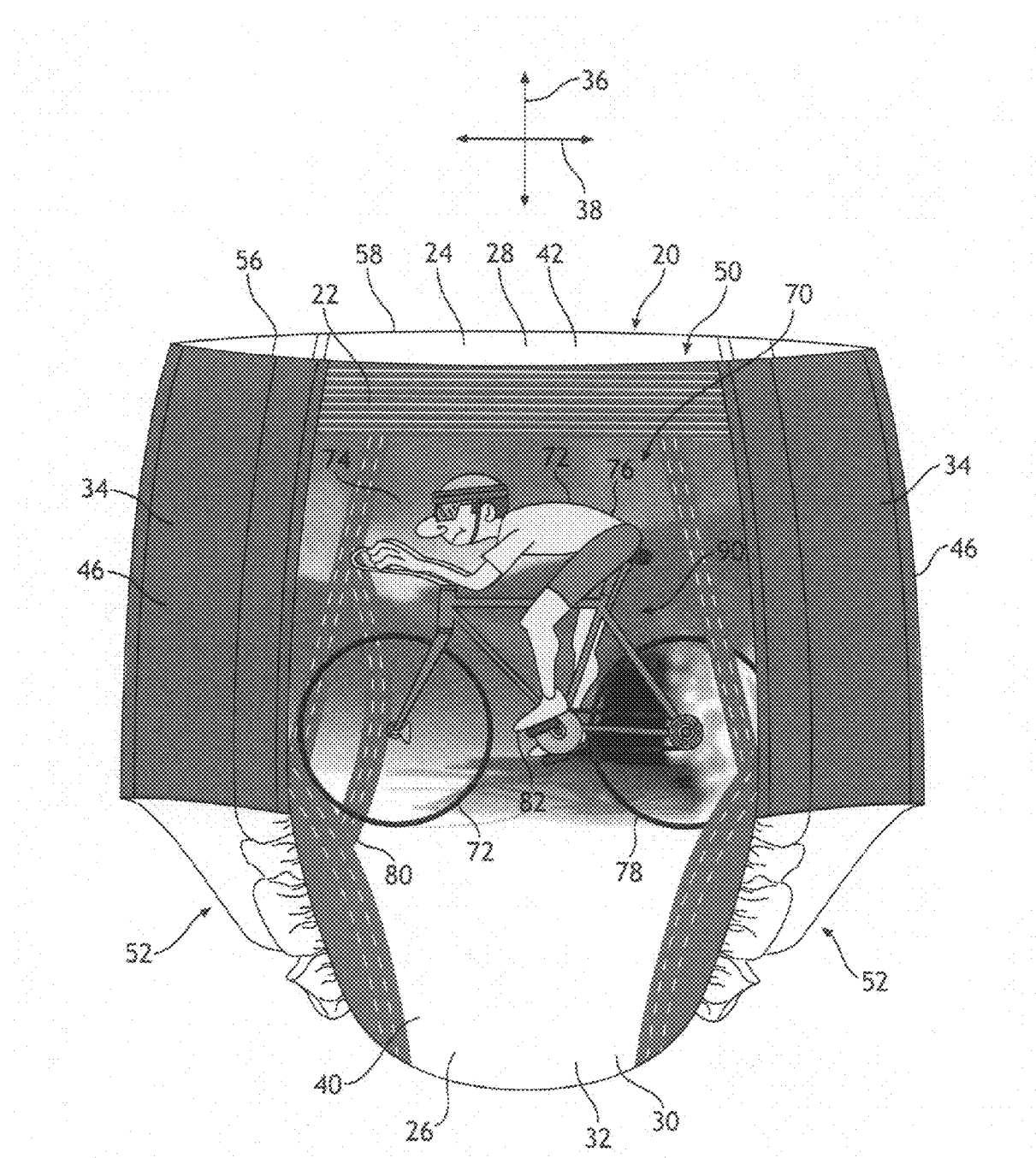
FIG. 1 representatively illustrates a front perspective view of a training pant having a multicolored scene graphic in accordance with one embodiment of the present invention.

Referring to FIG. 1, a training pant 20 is illustrated in a fully assembled condition. The training pant 20 defines a first or front waist region 22, a second or back waist region 24, a crotch region 26 positioned between and interconnecting the front and back waist regions, an inner surface 28 which is configured to contact the wearer, and an outer surface 30 opposite the inner surface which is configured to contact the wearer's clothing. The illustrated training pant 20 comprises an absorbent chassis 32 and a plurality of transversely opposed side panels 34. The absorbent chassis 32 and side panels 34 can be integrally formed or comprise two or more separate elements, as shown.

The training pant 20 defines a longitudinal direction 36, a transverse direction 38, a first or front longitudinal end edge 56, and a second or back longitudinal end edge 58. The first waist region 22 abuts the first longitudinal end edge 56, and the second waist region 24 abuts the second longitudinal end edge 58. "Longitudinal" and "transverse" have their customary meaning. The longitudinal axis lies in the plane of the article and is generally parallel to a vertical plane that bisects a standing wearer into left and right body halves when the article is worn. The transverse axis lies in the plane of the article generally perpendicular to the longitudinal axis.

The illustrated absorbent chassis 32 comprises an outer cover 40 and a bodyside liner 42 which is connected to the outer cover in a superposed relation. The absorbent chassis 32 also comprises an absorbent assembly (not shown) which is located between the outer cover 40 and the bodyside liner 42, and can optionally include a pair of containment flaps (not shown).

With the training pant 20 in a fully assembled condition as illustrated in FIG. 1, the front and back waist regions 22 and 24 are joined together by side seams 46 to define a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The side panels 34 comprise the portions of the training pant 20 which, when worn, are positioned on the side hip regions of the wearer. The longitudinal end edges 56 and 58 of the training pant 20 are configured to encircle the waist of the wearer when worn and provide the waist opening 50.

The absorbent chassis 32 is configured to contain and/or absorb any body exudates discharged from the wearer. For example, the absorbent chassis 32 desirably although not necessarily comprises a pair of containment flaps (not shown) which can be configured to provide a barrier to the transverse flow of body exudates. Suitable constructions and arrangements for the containment flaps are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 can include a front waist elastic member, a rear waist elastic member, and leg elastic members (not shown), as are known to those skilled in the art. Waist elastic members and leg elastic members can be operatively joined to the outer cover 40 and/or bodyside liner 42 of the training pant 20. Elastic members for the containment flaps, waist elastics and leg elastics can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the leg elastic members comprise a plurality of dry-spun coalesced multifilament spandex elastomeric threads sold under the trade name LYCRA® and available from E. I. Du Pont de Nemours and Company, Wilmington, Del.

The outer cover 40 has an exterior surface corresponding to the outer surface 30 of the training pant and an opposite interior surface (not shown). The outer cover 40 preferably comprises a material which is substantially liquid impermeable. The outer cover 40 can be a single layer of liquid impermeable material, but preferably comprises a multi-layer laminate structure in which at least one of the layers is liquid impermeable. In one example, the outer cover 40 is a two-layer laminate comprising a polymeric film layer and a nonwoven layer.

For additional detail regarding the construction of the pant, including the cover 40, the bodyside liner 42 and the absorbent assembly, reference may be made to published PCT Application No. PCT/US00/16542 (Pub. No. WO 00/76439), entitled "Absorbent Articles Having Wetness Indicating Graphics Incorporating A Training Zone, incorporated herein by reference to the extent consistent herewith.

Figure 2:
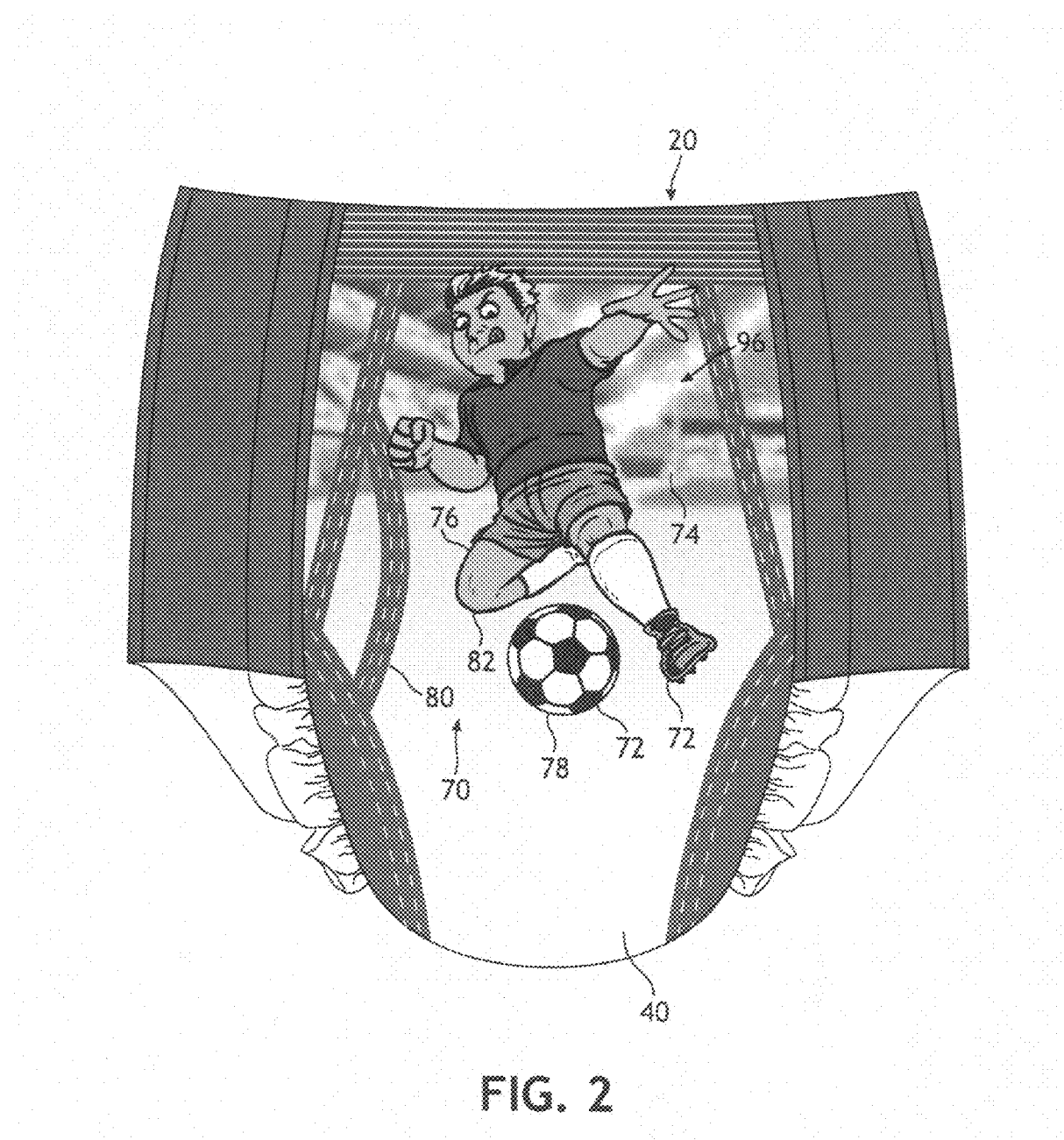
FIG. 2 representatively illustrates a front view of a training pant having a multicolored scene graphic in accordance with another embodiment of the present invention.
Figure 3:
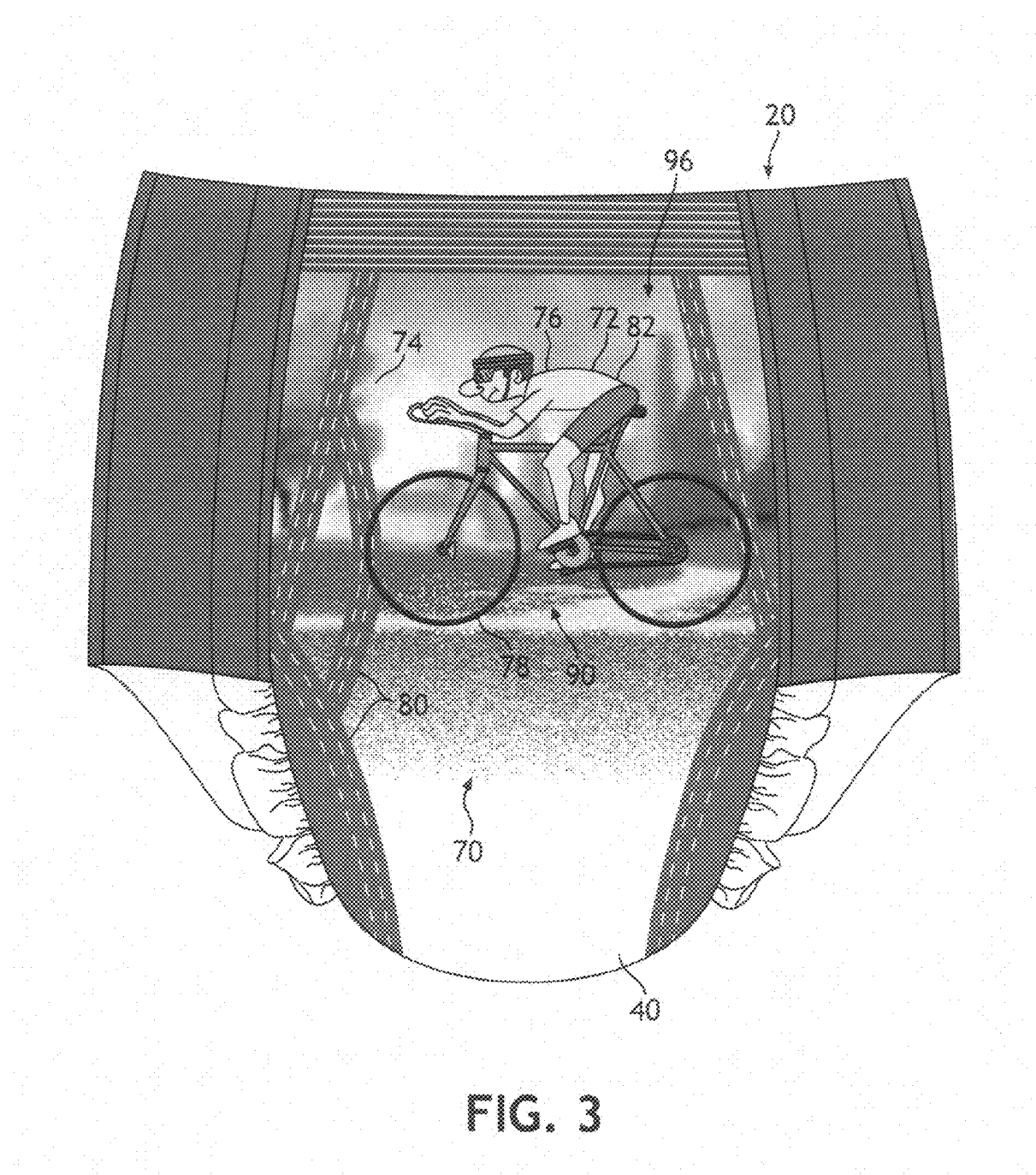
FIG. 3 representatively illustrates a front view of a training pant having a multicolored scene graphic in accordance with still another embodiment of the present invention.
Figure 4:
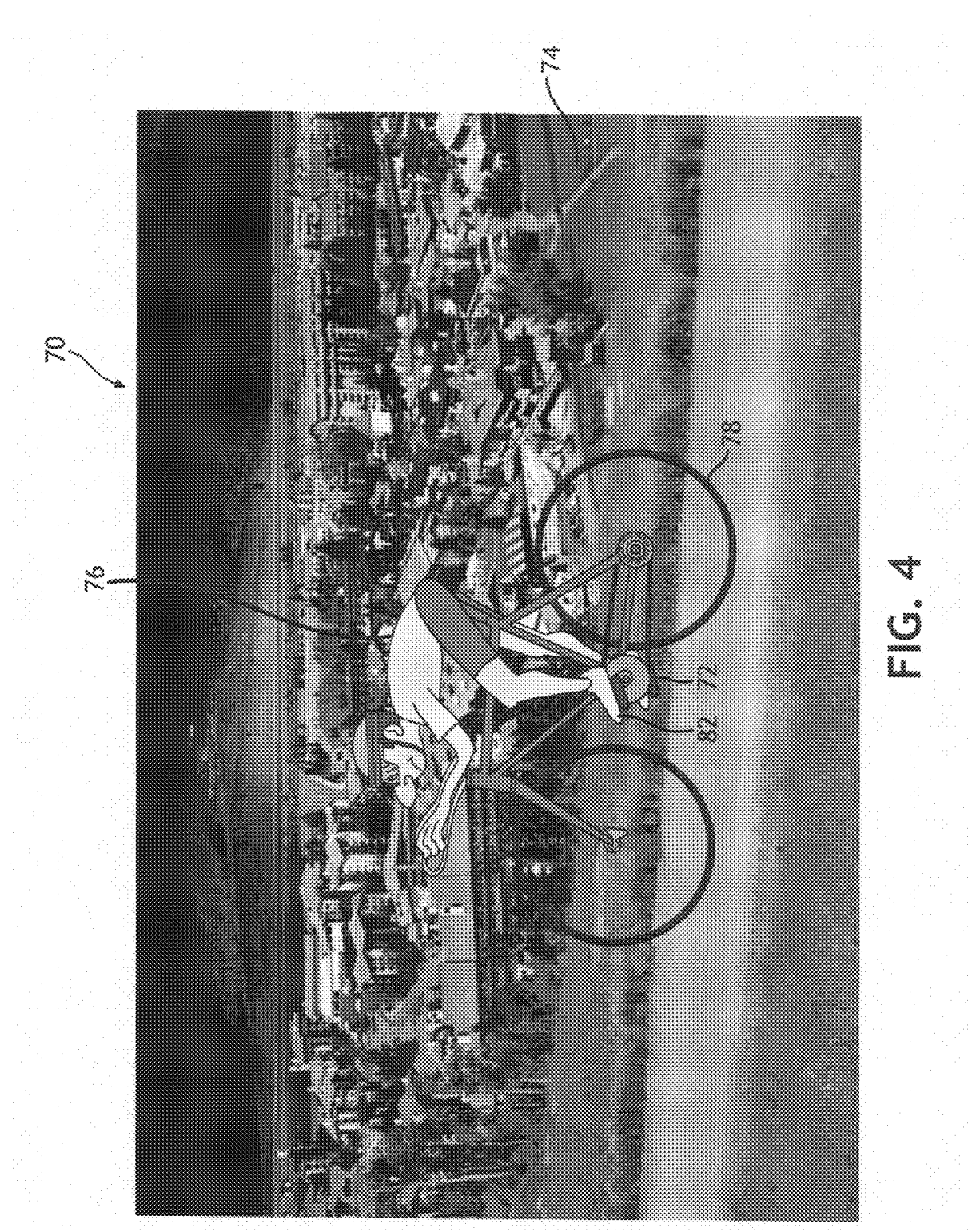
FIG. 4 representatively illustrates a multicolored scene graphic substantially devoid of any blurring.

Referring to the exemplary embodiments representatively illustrated in FIGS. 1-3, the disposable garment of the present invention includes a multicolored scene graphic 70 disposed thereon. The multicolored scene graphic includes at least one focal graphic 72 and at least one background graphic 74. The term "focal graphic" is used herein to refer to a graphic that is the center of interest or activity within the multicolored scene graphic, and that is intended to command the attention of a viewer. The focal graphic 72 can comprise any subject matter deemed desirable or suitable for the disposable garment on which it is disposed. The general term "graphic" is used herein to mean any design, pattern, or the like that is or becomes visible on an absorbent article, and can include pictorial images that consist of one or more pictures, text messages that consist of one or more alphanumeric symbols, or combinations thereof. The graphics discussed herein are suitably printed on any surface or substrate of the disposable garment that is at some point visible to a consumer, such as one or more layers of a multi-layered outer cover. In one example, the multicolored scene graphic is printed on either the polymeric film layer or the nonwoven layer in a two-layer outer cover.

In particular embodiments, representatively illustrated in FIGS. 1-7, 11-14 and 18-22, the focal graphic 72 can include at least one character graphic 76. The term "character graphic" is used herein to refer to a graphic containing an anthropomorphous image, and in particular an image having or suggesting human form or appearance which ascribes human motivations, characteristics or behavior to inanimate objects, animals, natural phenomena, cartoon characters, or the like. With respect to children's training pants, a character graphic would ideally be suitable for children's underwear and could be utilized to motivate children to wear the training pants and use a potty or toilet. To that end, a character graphic can be associated with popular characters in the media, advertising or well known in a particular culture. The role of the character graphic can be to help a child feel like a BIG KID® (a registered trademark of Kimberly-Clark Corporation) and to motivate them to become toilet trained. The character graphic 76 can also give parents and caregivers an interactive element for use during toilet training. Further, the character graphic may provide a source of comfort for the child and a buddy who reduces stress during the training period. The character graphic can, in particular embodiments, comprise a portion of the multicolored scene graphic that sets up a theme for the illustrated scene. As such, the character graphic can provide an opportunity for educational interaction between the child and the parent or caregiver. More specifically, the parent or caregiver can use the graphic story-line to make up a game or story for the purpose of toilet training progress.

Suitable character graphics 76 can include animals, people, inanimate objects, natural phenomena, cartoon characters, or the like that can or can not be provided with human features such as arms, legs, facial features or the like. For purposes of enhanced toilet training, it may be desirable for the character graphic to be familiar to the child, such as an identifiable cartoon character. The character graphics should at least be a type that the child can relate to, examples of which could include animals, toys, licensed characters, or the like. Character graphics can be made more personable and friendly to the child by including human-like features, human-like expressions, apparel, abilities, or the like. By way of illustration, an animal character graphic can be shown smiling, wearing clothing, or involved in or performing some activity, such as playing sports, fishing, driving, playing with toys, having a tea party, or the like. In particular embodiments, the character graphic can desirably be created to project an appearance that could be described as friendly, positive, non-intimidating, silly, independent, inspirational, active, expressive, dauntless and/or persevering.

As referenced above, the character graphic can in particular embodiments be involved in some activity, such as the activities representatively illustrated in FIGS. 1-7 and 11-14. In such embodiments, the multicolored scene graphic can further include at least one equipment graphic 78. The term "equipment graphic" is used herein to refer to a graphic that depicts an item that a character uses in some activity. Without wishing to be limited to the specific embodiments listed, examples of items which could constitute suitable equipment graphics, include: a racquet, bat, glove, ball, or other sporting equipment if the character is depicted as engaging in sports; a butterfly net if the character is shown as chasing butterflies; a fishing pole and a boat if the character is shown as fishing; potted plants or gardening tools if the character is shown as engaging in gardening; a telescope if the character is shown as star gazing; a racecar if the character is shown as auto racing; a sandbox is the character is shown as playing in the sand; a teapot if the character is shown as having a tea party; a bicycle if the character is shown riding a bicycle; or other suitable character graphic/equipment graphic combination.

In certain embodiments, the equipment graphic 78 is part of the focal graphic 72. In particular embodiments, both the character graphic 76 and the equipment graphic 78 are part of the focal graphic. The equipment graphic 78 can, but need not be, contiguous with the character graphic 76. For example, in the embodiments representatively illustrated in FIGS. 1, 3-8, and 12, a character graphic 76 is shown as being contiguous with an equipment graphic 78. That is, the character graphic and the equipment graphic at not spaced apart. In other embodiments, such as those representatively illustrated in FIGS. 2, 11, 13, and 14, a character graphic 76 is shown as being not contiguous with an equipment graphic 78. That is, the character graphic and the equipment graphic are spaced apart.

The multicolored scene graphic 70 further includes at least one background graphic 74. The term "background graphic" is used herein to refer to a graphic that depicts a suitable environment or setting for a particular focal graphic or graphics 72. In particular embodiments, the background graphic depicts an environment or setting suitable for an activity in which a character graphic is involved. By way of example, a background graphic 74 could include a road and surrounding land if a character is shown driving a car; a sports field or stadium if a character is shown engaging in a sport; a field if a character is shown chasing butterflies; a lake or river if a character is shown fishing; a garden if a character is shown engaging in gardening; a dining or living room, forest, or field if the character is shown as having a tea party; or other suitable background graphic/character graphic combination. The background graphic 74 can depict typical environmental elements, such as, for example, a blue sky, white clouds, or green grass. In certain embodiments, the background graphic 74 can be devoid of any character graphics and/or equipment graphics. In other embodiments, the background graphic can include character graphics and/or equipment graphics. The focal graphic or graphics 72 can be, but need not be, at least partially surrounded by the background graphic 74. For example, the background graphic 74 at least partially surrounds the focal graphic or graphics 72 in each of the exemplary embodiments of FIGS. 1-7, 11-14, and 18-22.

The disposable garment 20 can include graphics other than the focal graphic 72 and the background graphic 74. For example, the disposable garment 20 can include one or more garment-feature graphics 80, as representatively illustrated in FIGS. 1-3. The term "garment-feature graphic" is used herein to refer to graphics that are constructed to make a disposable garment appear more like real garments. Examples of garment-feature graphics include, but are not limited to, graphics that simulate functional components such as elastic leg bands, elastic waistbands, simulated "fly openings" for boys, ruffles or lace for girls, or other garment-like stitching or seaming; graphics that simulate a garment-like back label or a front label; or graphics that simulate a garment-like pocket. The terms "focal graphic" and "background graphic" as used herein do not refer to garment-feature graphics. In particular embodiments, one or more garment-feature graphics are not blurry.

In particular embodiments, it is desirable that the focal graphic "stand out" from the background graphic. It has been discovered that, if one or more portions of the background graphic are constructed to appear "blurry," and if one or more portions of the focal graphic are constructed to appear relatively less "blurry," the focal graphic is made to "stand out" in a desirable manner. For example, if one or more portions of a character graphic are constructed to appear relatively non-"blurry" as compared to a relatively "blurry" background graphic, the character graphic advantageously "stands out" from the background graphic, and can deliver an enhanced conspicuousness to a character graphic disposed on a disposable garment, such as a child's training pant.

It has been discovered that, by manipulation of particular attributes of particular portions of multicolored scene graphics, the aforementioned blurring effect can, in particular embodiments, be achieved. By way of background, colors are frequently characterized by three attributes: hue, saturation, and brightness or Value. "Hue," as used herein and as generally understood in the art, refers to the attribute of colors that permits them to be classed as red, yellow, green, blue, or an intermediate between any contiguous pair of these colors, as determined by the dominant wavelength of the light. "Saturation," as used herein and as generally understood in the art, refers to the degree of difference of a color from a gray of the same lightness or brightness, or, stated another way, to the vividness of the hue. "Brightness" and "Value," as used herein and as generally understood in the art, refer to the attribute of a color that represents its similarity to one of a series of achromatic colors ranging from very dim (dark) to very bright (dazzling). An "achromatic" color is one that possesses no hue, and involves only black, gray, or white.

By constructing particular portions, such as color transition regions, of the focal graphic and/or the background graphic to exhibit specific gradient characteristics in one or more of the three above-referenced attributes, the conspicuousness of the focal graphic can be enhanced relative to the background graphic. "Color transition region" as used herein generally refers to an edge or edge-like portion within a graphic or image across which a color visually changes, in contrast to a section or region which is visually relatively solid, flat, or otherwise constant in color. As explained in detail below, configuring particular color transition regions to exhibit certain maximum gradients or ranges of maximum gradients in hue, saturation, and/or brightness/value can produce the desired arrangement of blurry and non-blurry images. Stated in the converse, and also as explained in detail below, configuring particular color transition regions within a graphic or image, to exhibit particular characteristic transition widths or ranges of characteristic transition widths in hue, saturation, and/or brightness/value can produce the desired arrangement of blurry and non-blurry images.

In particular embodiments, the focal graphic comprises at least one color transition region exhibiting a color hue gradient of at least about 0.3, more particularly at least about 0.4, still more particularly at least about 0.5, still more particularly at least about 0.6, still more particularly at least about 0.7, still more particularly at least about 0.8, still more particularly at least about 0.9, still more particularly at least about 1.0, still more particularly at least about 1.1, still more particularly at least about 1.2, still more particularly at least about 1.3, still more particularly at least about 1.4, still more particularly at least about 1.5, still more particularly at least about 1.6, still more particularly at least about 1.7, and still more particularly at least about a 1.8 normalized hue angle per millimeter.

In particular embodiments, the background graphic comprises at least one color transition region exhibiting a color hue gradient of at most about 1.5, more particularly at most about 1.4, still more particularly at most about 1.3, still more particularly at most about 1.2, still more particularly at most about 1.1, still more particularly at most about 1.0, still more particularly at most about 0.9, still more particularly at most about 0.8, still more particularly at most about 0.7, still more particularly at most about 0.6, still more particularly at most about 0.5, still more particularly at most about 0.4, and still more particularly at most about a 0.3 normalized hue angle per millimeter.

In particular embodiments, the focal graphic comprises at least one color transition region exhibiting a characteristic hue transition width of at most about 2.6, more particularly at most about 2.4, still more particularly at most about 2.0, still more particularly at most about 1.8, still more particularly at most about 1.6, still more particularly at most about 1.4, still more particularly at most about 1.2, still more particularly at most about 1.0, still more particularly at most about 0.8, still more particularly at most about 0.6, still more particularly at most about 0.4, still more particularly at most about 0.3, and still more particularly at most about 0.2 millimeters.

In particular embodiments, the background graphic comprises at least one color transition region exhibiting a characteristic hue transition width of at least about 0.3, more particularly at least about 0.4, still more particularly at least about 0.5, still more particularly at least about 0.6, more particularly at least about 0.8, still more particularly at least about 1.0, still more particularly at least about 1.5, still more particularly at least about 2.0, still more particularly at least about 2.5, still more particularly at least about 3.0, still more particularly at least about 3.5, still more particularly at least about 4.0, still more particularly at least about 4.5, still more particularly at least about 5.0, still more particularly at least about 5.5, and still more particularly at least about 6.0 millimeters.

In particular embodiments, the focal graphic comprises at least one color transition region exhibiting a color saturation gradient of at least about 0.7, more particularly at least about 1.0, still more particularly at least about 1.5, still more particularly at least about 2.0, still more particularly at least about 2.5, still more particularly at least about 3.0, still more particularly at least about 3.5, and still more particularly at least about 4.0 normalized saturation units per millimeters.

In particular embodiments, the background graphic comprises at least one color transition region exhibiting a color saturation gradient of at most about 4.0, more particularly at most about 3.5, still more particularly at most about 3.0, still more particularly at most about 2.5, still more particularly at most about 2.0, still more particularly at most about 1.5, still more particularly at most about 1.0, and still more particularly at most about 0.5 normalized saturation units per millimeters.

In particular embodiments, the focal graphic comprises at least one color transition region exhibiting a characteristic saturation transition width of at most about 1.4, still more particularly at most about 1.2, still more particularly at most about 1.0, still more particularly at most about 0.8, still more particularly at most about 0.6, still more particularly at most about 0.4, still more particularly at most about 0.35, still more particularly at most about 0.3, still more particularly at most about 0.25, and still more particularly at most about 0.2 millimeters.

In particular embodiments, the background graphic comprises at least one color transition region exhibiting a characteristic saturation transition width of least about of at least about 0.5, more particularly at least about 0.6, more particularly at least about 0.7, more particularly at least about 0.8, more particularly at least about 1.0, still more particularly at least about 1.5, still more particularly at least about 2.0, still more particularly at least about 2.5, still more particularly at least about 3.0, still more particularly at least about 3.5, still more particularly at least about 4.0, and still more particularly at least about 4.5 millimeters.

In particular embodiments, the focal graphic comprises at least one color transition region exhibiting a color value gradient of at least about 1.5, still more particularly at least about 2.0, still more particularly at least about 2.5, still more particularly at least about 3.0, still more particularly at least about 3.5, still more particularly at least about 4.0, still more particularly at least about 4.5, and still more particularly at least about 5.0 normalized value units per millimeter.

In particular embodiments, the background graphic comprises at least one color transition region exhibiting a color value gradient of at most about 1.5, more particularly at most about 1.4, still more particularly at most about 1.3, still more particularly at most about 1.2, still more particularly at most about 1.1, still more particularly at most about 1.0, still more particularly at most about 0.9, still more particularly at most about 0.8, still more particularly at most about 0.7, still more particularly at most about 0.6, still more particularly at most about 0.5, still more particularly at most about 0.4, still more particularly at most about 0.3, and still more particularly at most about 0.2 normalized value units per millimeter.

In particular embodiments, the focal graphic comprises at least one color transition region exhibiting a characteristic value transition width of at most about 2.6, more particularly at most about 2.4, still more particularly at most about 2.0, still more particularly at most about 1.8, still more particularly at most about 1.6, still more particularly at most about 1.4, still more particularly at most about 1.2, still more particularly at most about 1.0, still more particularly at most about 0.8, still more particularly at most about 0.6, still more particularly at most about 0.4, and still more particularly at most about 0.2 millimeters.

In particular embodiments, the background graphic comprises at least one color transition region exhibiting a characteristic value transition width of least about 0.6, more particularly at least about 0.8, still more particularly at least about 1.0, still more particularly at least about 1.5, still more particularly at least about 2.0, still more particularly at least about 2.5, still more particularly at least about 3.0, still more particularly at least about 3.5, still more particularly at least about 4.0, still more particularly at least about 4.5, still more particularly at least about 5.0, and still more particularly at least about 5.5 millimeters.

The various color-attribute gradients discussed above can exist alone or in combination with others within a graphic. For example, a color transition region within a focal graphic can exhibit a particular hue gradient, a saturation gradient, a value (brightness) gradient, or a combination of two or all three color-attribute gradients. Similarly, at least one portion of a background graphic can exhibit a particular hue gradient, a saturation gradient, a brightness gradient, or a combination of two or all three color-attribute gradients. Likewise, a color transition region within a focal graphic can exhibit a particular characteristic transition width in two or more color attributes, and a color transition region within a background graphic can exhibit a particular characteristic transition width in two or more color attributes.

In particular embodiments, a minimum percentage level of the total area of the background graphic includes no color transition regions having a color hue gradient greater than a specified level, or having a characteristic hue transition width less than a specified level. The specified levels can be any of the hue gradient maximum levels or characteristic hue transition width minimum levels previously recited as suitable for background graphics. In particular embodiments, the percentage level of the total area of the background graphic having no such color transition regions can be at least about 50%, more particularly at least about 60%, still more particularly at least about 70%, still more particularly at least about 80%, still more particularly at least about 90%, still more particularly at least about 95%, and still more particularly at least about 99%.

In particular embodiments, a minimum percentage level of the total area of the focal graphic includes no color transition region having a color hue gradient less than a specified level, or a having a characteristic hue transition width greater than a specified level. The specified levels can be any of the hue gradient minimum levels or characteristic hue transition width maximum levels previously recited as suitable for focal graphics. In particular embodiments, the percentage level of the total area of the focal graphic having no such color transition regions can be at least about 50%, more particularly at least about 60%, still more particularly at least about 70%, still more particularly at least about 80%, still more particularly at least about 90%, still more particularly at least about 95%, and still more particularly at least about 99%.

In particular embodiments, a minimum percentage level of the total area of the background graphic includes no color transition regions having a color saturation gradient greater than a specified level, or having a characteristic saturation transition width less than a specified level. The specified levels can be any of the saturation gradient maximum levels or characteristic saturation transition width minimum levels previously recited as suitable for background graphics. In particular embodiments, the percentage level of the total area of the background graphic having no such color transition regions can be at least about 50%, more particularly at least about 60%, still more particularly at least about 70%, still more particularly at least about 80%, still more particularly at least about 90%, still more particularly at least about 95%, and still more particularly at least about 99%.

In particular embodiments, a minimum percentage level of the total area of the focal graphic includes no color transition region having a color saturation gradient less than a specified level, or a having a characteristic saturation transition width greater than a specified level. The specified levels can be any of the saturation gradient minimum levels or characteristic saturation transition width maximum levels previously recited as suitable for focal graphics. In particular embodiments, the percentage level of the total area of the focal graphic having no such color transition regions can be at least about 50%, more particularly at least about 60%, still more particularly at least about 70%, still more particularly at least about 80%, still more particularly at least about 90%, still more particularly at least about 95%, and still more particularly at least about 99%.

In particular embodiments, a minimum percentage level of the total area of the background graphic includes no color transition regions having a color value gradient greater than a specified level, or having a characteristic value transition width less than a specified level. The specified levels can be any of the value gradient maximum levels or characteristic value transition width minimum levels previously recited as suitable for background graphics. In particular embodiments, the percentage level of the total area of the background graphic having no such color transition regions can be at least about 50%, more particularly at least about 60%, still more particularly at least about 70%, still more particularly at least about 80%, still more particularly at least about 90%, still more particularly at least about 95%, and still more particularly at least about 99%.

In particular embodiments, a minimum percentage level of the total area of the focal graphic includes no color transition region having a color value gradient less than a specified level, or a having a characteristic value transition width greater than a specified level. The specified levels can be any of the value gradient minimum levels or characteristic value transition width maximum levels previously recited as suitable for focal graphics. In particular embodiments, the percentage level of the total area of the focal graphic having no such color transition regions can be at least about 50%, more particularly at least about 60%, still more particularly at least about 70%, still more particularly at least about 80%, still more particularly at least about 90%, still more particularly at least about 95%, and still more particularly at least about 99%.

It has in particular embodiments been found effective to outline at least a portion of the focal graphic 72 with a dark-colored border 82 to further increase the conspicuousness of the focal graphic. For example, at least about 50%, more particularly about 60%, still more particularly about 70%, still more particularly about 80%, yet more particularly about 90%, and still more particularly about 99% of the periphery of the focal graphic 72 (or peripheries if the focal graphic comprises two or more spaced-apart components) is bordered by a dark color border 82. If the focal graphic 72 includes both a character graphic 76 and an equipment graphic 78, one or both of them can include such a border. In particular embodiments, such as those representatively illustrated in FIGS. 1-7 and 11-14, the focal graphic includes both a character graphic and an equipment graphic, and 100% of the periphery of the focal graphic is bordered by a dark color border 82.

In particular embodiments, the border 82 is about 0.2 mm wide, more particularly about 0.5 mm wide, still more particularly about 1 mm wide, yet more particularly about 2 mm wide, and still more particularly about 3 mm wide. It should be noted that the foregoing border widths are exemplary only. Additionally, the term "dark color" as used herein means a color having a brightness or value level of at most about 0.25, and more particularly at most about 0.1. Although a variety of color hues may be used to border the focal graphic, examples of suitable colors include black, dark gray, dark blue, dark purple, dark green, and dark brown.

It has further been discovered that certain objectives of the present invention can be achieved by providing a focal graphic and/or background graphic with one or more blur effects. In one example, at least a part of the total area of the background graphic exhibits a Gaussian blur effect (represented in the Figures with reference numeral 90), such as, for example, a Gaussian blur effect of at least about 2 pixels, more particularly at least about 3 pixels, still more particularly at least about 4 pixels, still more particularly at least about 5 pixels, still more particularly at least about 8 pixels (representatively illustrated in FIGS. 5 and 14) still more particularly at least about 10 pixels, still more particularly at least about 15 pixels, still more particularly at least about 20 pixels (representatively illustrated in FIGS. 6, 11, and 12), still more particularly at least about 25 pixels, still more particularly at least about 30 pixels, and still more particularly at least about 40 pixels (representatively illustrated in FIGS. 7 and 13). It can be desirable in particular embodiments that portions of the background be blurred, but not "over-blurred." Thus, in certain embodiments, at least a part of the total area of the background graphic exhibits a Gaussian blur effect that is at most about 40 pixels, more particularly at most about 30 pixels, more particularly at most about 20 pixels, more particularly at most about 15 pixels, more particularly at most about 11 pixels, more particularly at most about 9 pixels, and still more particularly at most about 7 pixels.

Figure 18:
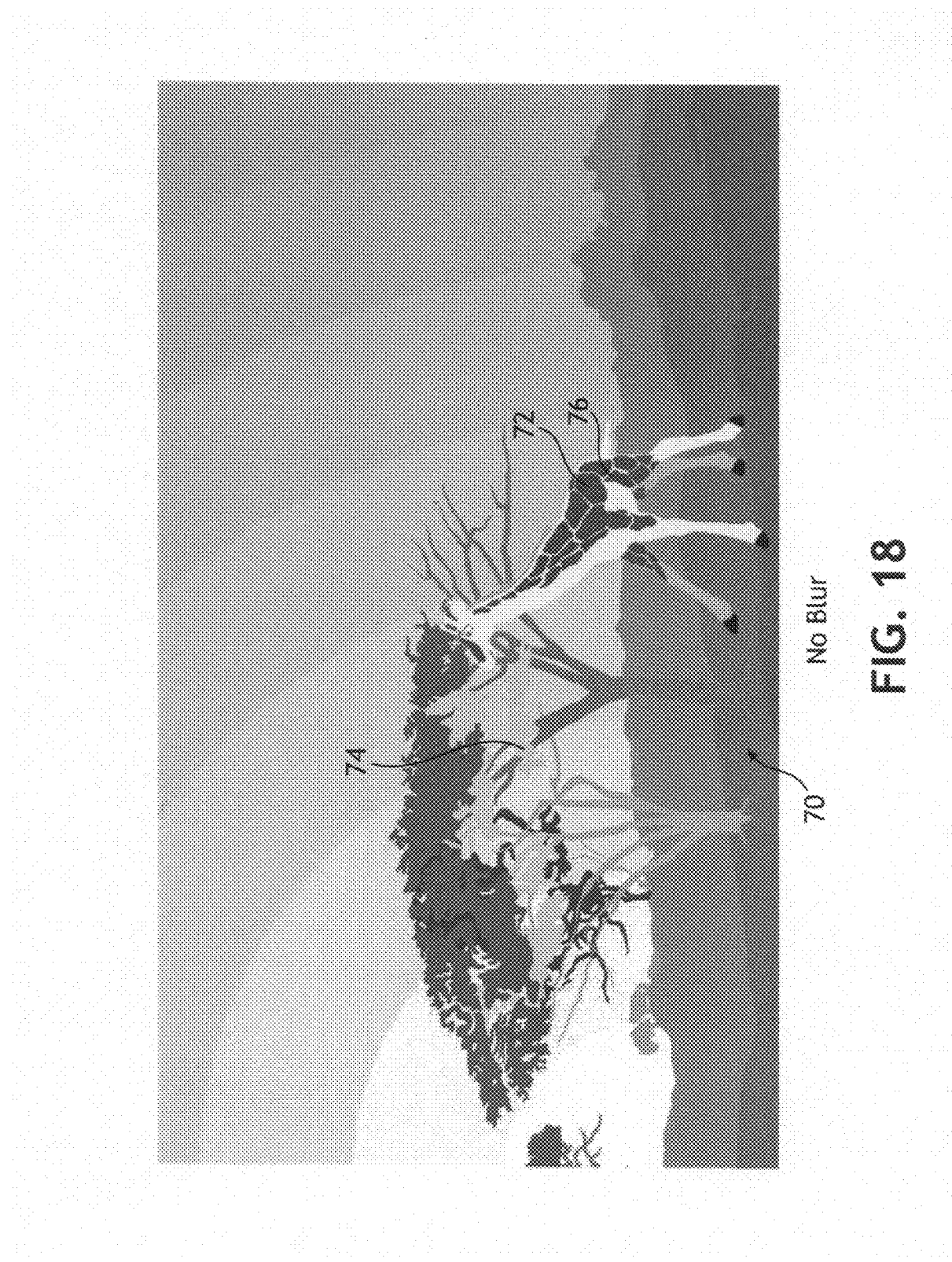
FIG. 18 representatively illustrates a multicolored scene graphic substantially devoid of any blurring.
Figure 19:
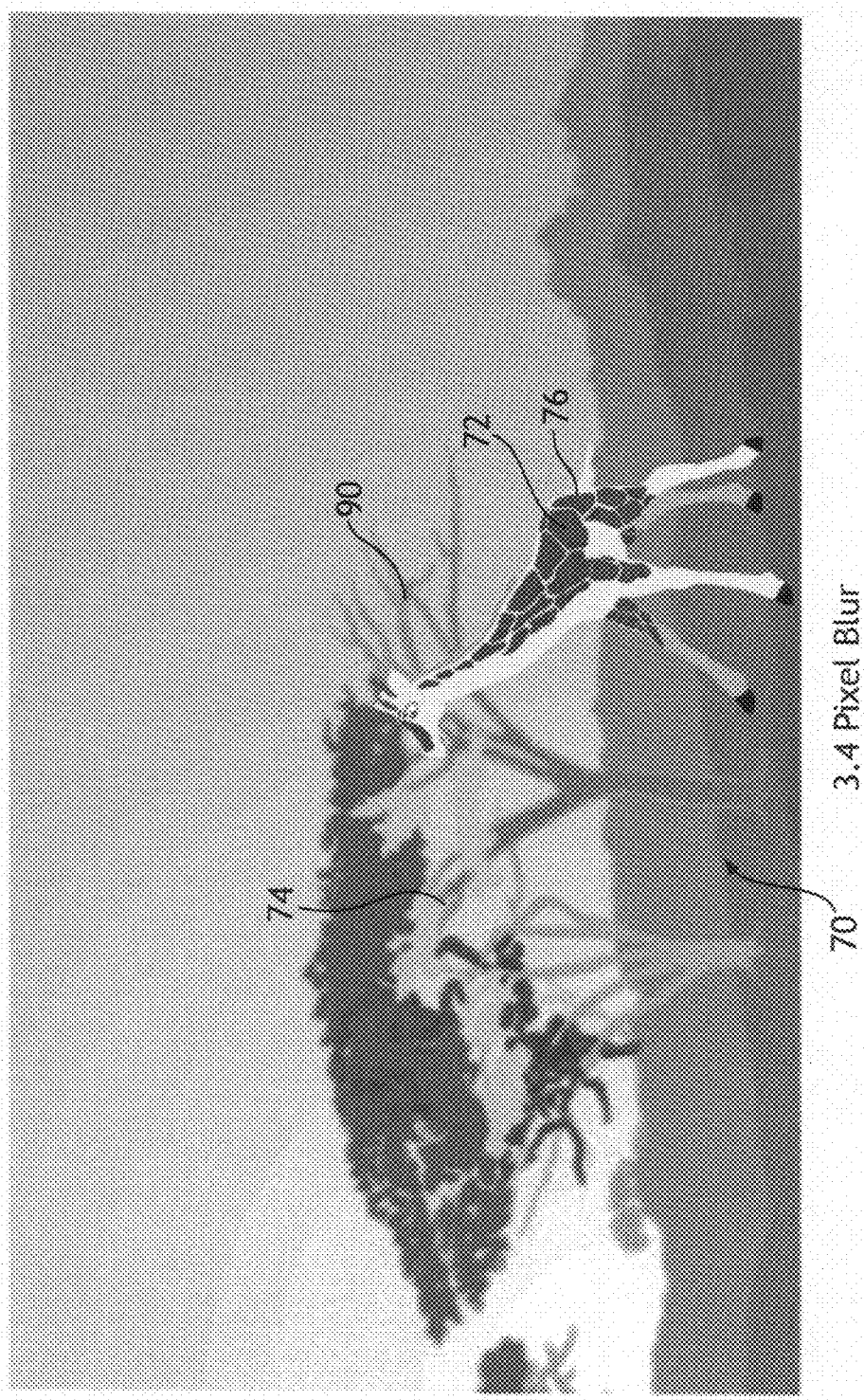
FIG. 19 representatively illustrates a multicolored scene graphic in accordance with one embodiment of the present invention.
Figure 20:
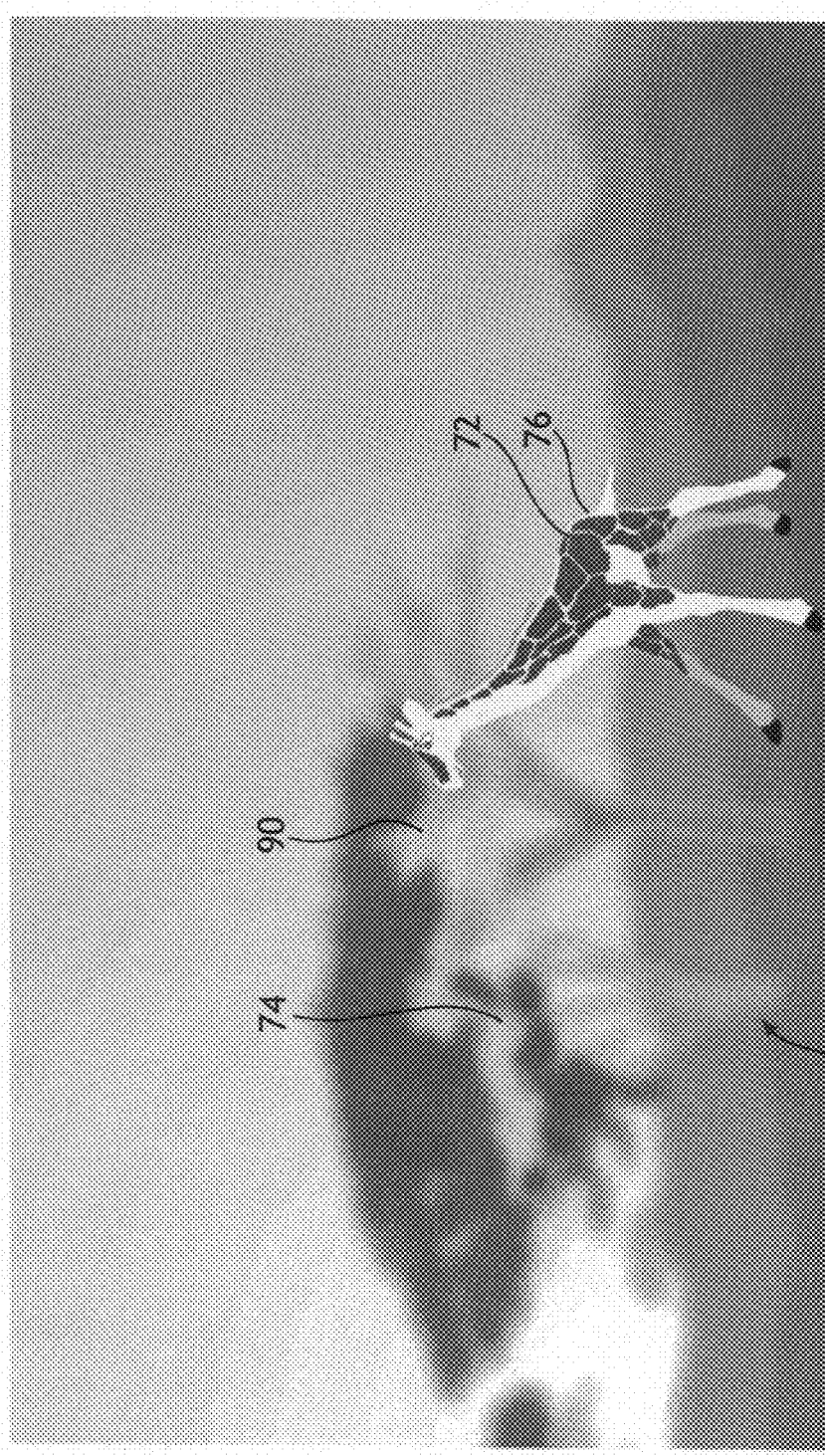
FIG. 20 representatively illustrates a multicolored scene graphic in accordance with another embodiment of the present invention.
Figure 21:
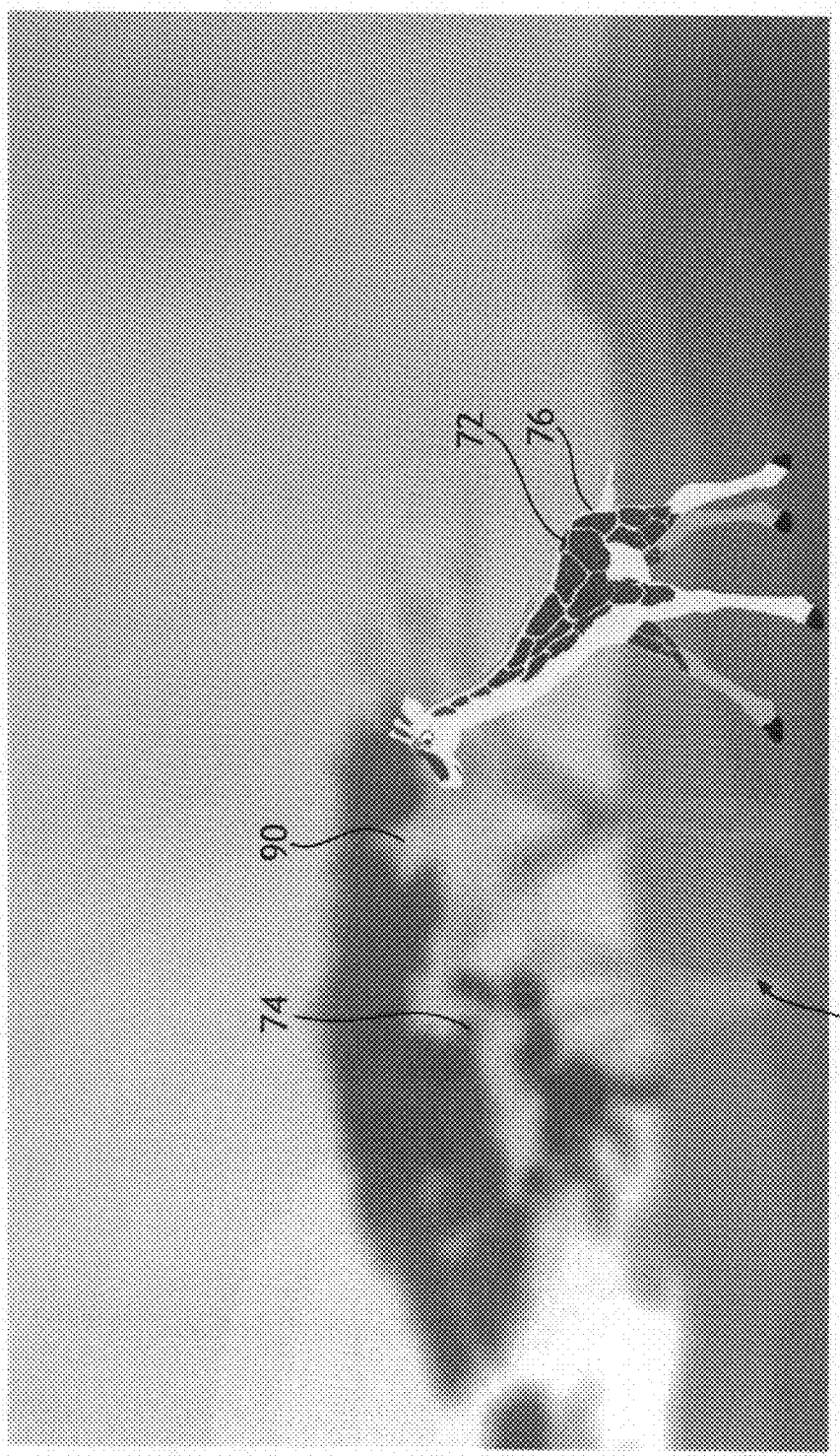
FIG. 21 representatively illustrates a multicolored scene graphic in accordance with yet another embodiment of the present invention.
Figure 22:
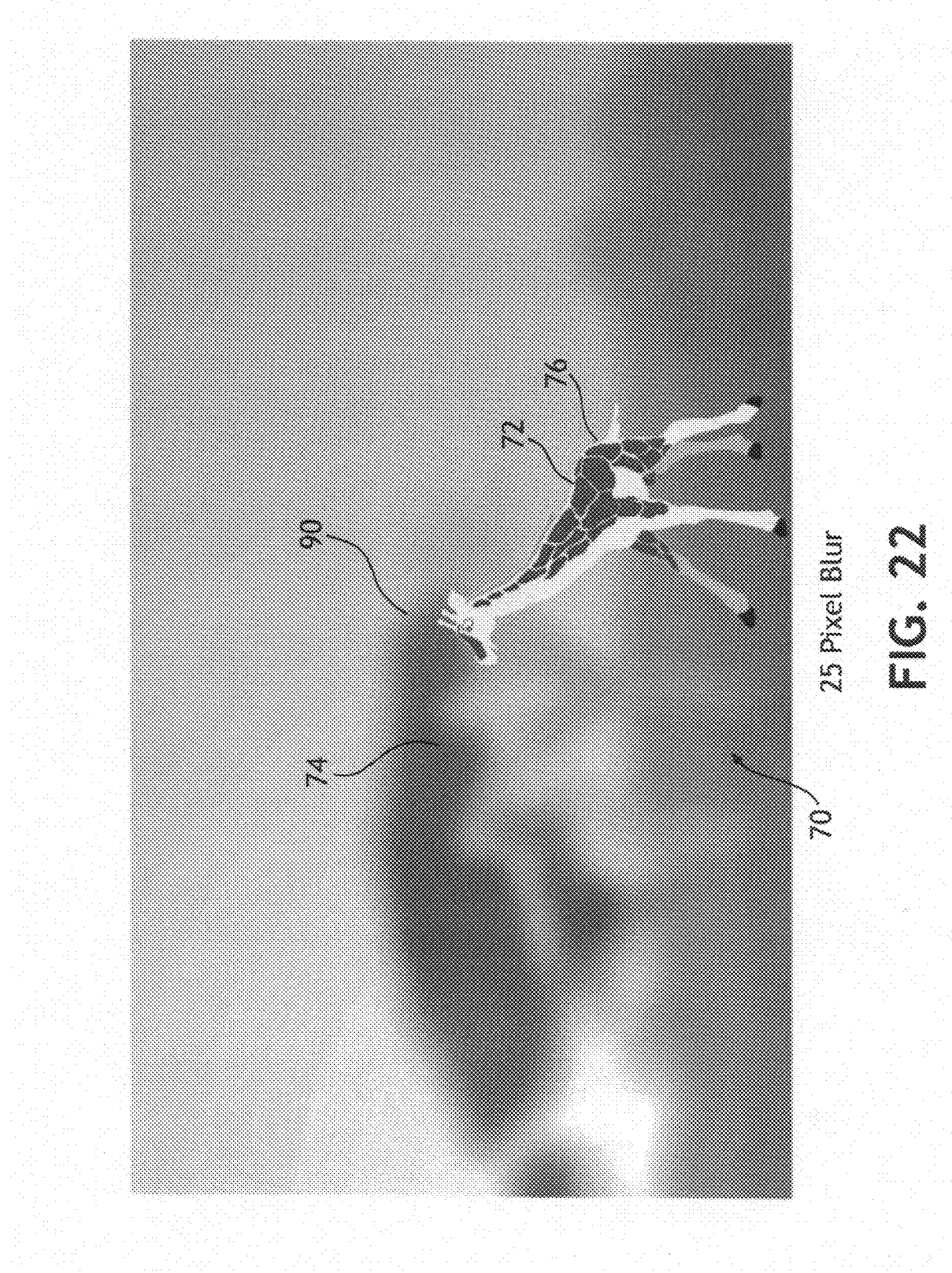
FIG. 22 representatively illustrates a multicolored scene graphic in accordance with yet another embodiment of the present invention.

Additional reference is made to the exemplary embodiments of FIGS. 18-22 to illustrate the effect of various pixel-count blur effects. FIGS. 18-22 each include a substantially unblurred focal graphic 72, and each includes a background graphic 74. The background graphic 74 of FIG. 18 is substantially unblurred. The background graphics 74 of FIGS. 19-22 become successively blurrier as one progresses from FIG. 19 to FIG. 22. The background graphics of FIGS. 19, 20, 21, and 22 were created using a Gaussian blur effect of 3.4 pixels, 6.7 pixels, 11 pixels, and 25 pixels, respectively. In certain embodiments, the background graphic of FIG. 22 (25 pixels) is undesirably "over-blurred."

The part of the total area of the background graphic exhibiting a Gaussian blur can be expressed in terms of a percentage of the total area of the background graphic, and in particular embodiments the area of such part is at least about 50%, more particularly at least about 60%, still more particularly at least about 70%, still more particularly at least about 80%, still more particularly at least about 90%, still more particularly at least about 95%, and still more particularly at least about 99%. The term "Gaussian blur effect" as used herein means a blur that is perceptually substantially similar to a blur imparted to an unblurred image via a Gaussian blur application mechanism. Examples of mechanisms suitable for imparting a Gaussian blur effect to an unblurred image include digital image software such as PhotoShop® (such as version 7.0) and Illustrator® (such as version 10), both software packages available from Adobe Systems Inc. of San Jose, Calif., U.S.A. However, it is understood that the scope of the present invention is not limited by the use or non-use of these exemplary mechanisms.

In particular embodiments, representatively illustrated in FIGS. 5-7 and 11-13, at least a part of the focal graphic is accompanied by a motion blur effect (represented in the Figures with reference numeral 92), such as, for example, a motion blur effect of at least about 10 pixels, more particularly at least about 20 pixels, still more particularly at least about 30 pixels, still more particularly at least about 50 pixels, still more particularly at least about 100 pixels, still more particularly at least about 200 pixels, still more particularly at least about 500 pixels, and still more particularly at least about 900 pixels (representatively illustrated in FIGS. 5-7 and 12-13). In particular embodiments, a motion blur effect 92 can extend in a relatively straight manner (representatively illustrated in FIGS. 5-7 and 13), can extend along a curve to create a radial blur effect ((represented in FIG. 11 with reference numeral 94), and/or can be configured so as to create a perspective effect (representatively illustrated in FIG. 12).

In yet another example, representatively illustrated in FIGS. 2, 3, 9, and 10, at least a part of the background graphic 74 exhibits a color cutback effect (represented in the Figures with reference numeral 96). "Color cutback effect" as used herein refers to a faded or dulled colored graphic that is perceptually substantially similar to a fading or dulling imparted to an image via a cutback application mechanism. In particular examples, the percent of color cutback is at least about 25%, more particularly at least about 50% (representatively illustrated in FIG. 9), and still more particularly at least about 75% (representatively illustrated in FIG. 10). Examples of mechanisms suitable for imparting a cutback effect to an image include digital image software such as PhotoShop® (such as version 7.0) and Illustrator® (such as version 10), both software packages available from Adobe Systems Inc. of San Jose, Calif., U.S.A.

As various changes could be made in the above exemplary embodiments, without departing from the scope of the invention, it is intended that all matter contained in the above description and shown in the accompanying drawings shall be interpreted as illustrative and not in a limiting sense.

When introducing elements of the invention or particular embodiment(s) thereof, the articles "a", "an", "the" and "said" are intended to mean that there are one or more of the elements. The terms "comprising", "including" and "having" are intended to be inclusive and mean that there may be additional elements other than the listed elements.

Quantitative Analysis of Color Transition Regions

As an introduction to understanding calorimetric quantification by image analysis, it is useful to consider first the quantitative measurement of brightness which is called grey densitometry. An imaging system composed of a monochrome (e.g. black/white) camera captures an image of an object; that is, it spatially records light within a two dimensional field of view onto film or an imaging array. In digital densitometry, light is converted to electrical signals which are then converted to a digital representation or levels. Traditionally, black is assigned 0 and white is 255 on an 8-bit scale, but the actual light signal range that is captured is defined by the camera's dynamic range as well as signal gain, offset, filters, lens f/stop, and other means. Therefore, the measured brightness values between 0-255 are acquisition system and illumination dependent.

Two important references are necessary in grey-densitometry. First, a dark-field is required to account for dark current of the camera and electronics which is taken when the light path to the camera is closed. Second, a flat-field is required using a white, defocused background to correct for non-uniform illumination. During the flat-field procedure, the illumination level is adjusted so that the mean intensity of the field is 190 (out of 255 levels). Doing so maximizes the useful dynamic range of the camera and will typically keep saturated pixels below 1%. Saturated pixels are undesirable since they describe all light intensities above a certain level as 255, and therefore should be minimized.

Having briefly described grey-level densitometry, its relevance to color quantification will be discussed. Scientific color cameras typically decompose color information into red, green, and blue channels which are typically 8-bit (0-255). In addition to the dark-field and flat-field corrections above, these channels are often adjusted by a white reference using the same flat-field so that the means of the red, green, and blue channels are all equal.

The RGB channels, or coordinates, of an electronic image can be converted to a color space, such as by a suitable color conversion or image analysis program. For example, a conversion to the hue, saturation, value (HSV) space can be accomplished by Matlab® 6.5 (Release 13, Service Pack 1) with the Imaging Processing Toolbox 4.0, software available from Mathworks Inc. Other color conversion and image analysis programs are available and known in the art and that perform the same or similar conversions (e.g., hue-saturation-intensity or hue-saturation-luminosity). FIG. 15 shows example normalized RGB values and the corresponding normalized HSV values for white, green, red, pink, gray, and black. The hue is the angular coordinate proceeding from red (H=0) to yellow, green, cyan, blue, magenta, and back to red as H approaches 1. When the saturation is 0, the colors are unsaturated (shades of gray) and the hue coordinate is meaningless. As the Value increases, the brightness increases.

The colorimetric differences between colors can be posed in terms of HSV coordinate differences—that is, differences between hue, saturation, and/or value. With normalized quantities, the maximum coordinate difference between any two colors is 1 (or hue difference of 180 degrees). Alternatively, the calorimetric difference can be expressed as a functionality of the differences, such as the Euclidean distance form below:

$$d = \sqrt{(\Delta H)^2 + (\Delta S)^2 + (\Delta V)^2}$$

Alternatively, the colorimetric difference can be based on a conversion of colors to an appropriate CIE colorspace (e.g., L*a*b or XYZ) using the individual difference or a function of some or all of the differences.

As discussed earlier, an edge in a color graphic can be posed as a color transition region where the hue, saturation, and/or value (or brightness) can change over some distance. The color transition can be characterized by a slope, or, more generally, by the gradient of color change. In-focus, or "crisp," images will have well defined edges with relatively high-magnitude gradients in the hue, saturation, and/or value channels. Out-of-focus, or "blurry," images will have broader, smoothed out, edges which will have broad, relatively low-magnitude gradients in one or more of the channels. Therefore, the calculated gradientmagnitude images for each channel in a color transition region provide information relating to the degree of perceived blur across the color transition region.

Color transitions can be characterized for an entire image or any particular region of interest ("ROI") within a larger image. The digital image may be created with software, or be acquired through imaging or scanning. The minimum size (in pixels) and shape or a particular ROI is defined by the formulation of the gradient, and hence typically has an aspect ratio of approximately 1 (e.g., a square or circle), but any size or shape ROI that meets the gradient formulation requirements can be used. The gradient used herein is the GRADIENT function employed by the Matlab® software reference earlier, which uses the centered pixel difference (i.e., a 3-pixel wide structuring element) and returns the gradient in the 'x' and 'y' directions. The magnitude of the gradient, MG(f), is then calculated as follows:

$$MG(f) = |\nabla f| = \sqrt{\left(\frac{df}{dx}\right)^2 + \left(\frac{df}{dy}\right)^2}$$

where 'f' may be hue, saturation, or value (brightness). For example, the magnitude of the brightness gradient is represented by MG(V). The angular representation of hue requires a modification of the gradient calculation to account for the fact that 359 degrees and 1 degree are only 2 degrees apart. Note that the hue gradient was only calculated for pixels whose saturation was greater than 0.01, since the hue value is meaningless for unsaturated (i.e. achromatic) colors. Each MG(f) can be used individually, sequentially, or as a composite of 2 or more individual MG(f), such as the norm (i.e. Euclidean distance), maximum, normal or weighted sum, or other functionality.

For any ROI containing a color transition, the calculated MG(f) will characterize the transition in terms of how fast the color changes its hue, saturation, or value traversing across the edge. The MG(f) contains a distribution of measurements, and the maximum MG(f) provides one metric to discriminate between the focal and the background graphic. Other statistics, such as, for example, the mean, median, or 90% maximum, could also be used.

Figure 16:
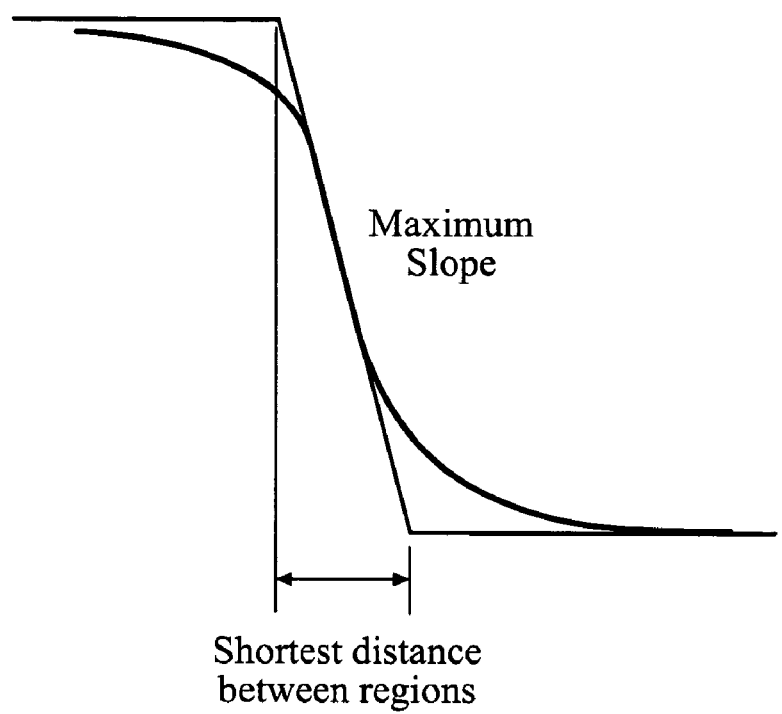
FIG. 16 representatively characterizes a color attribute gradient across a hypothetical color transition region.

The maximum MG(f) translates to the minimum distance between the local maximum and minimum of some color attribute in two different color regions, whether it be hue, saturation, or value. In FIG. 16, a color attribute changes across a color transition region as movement is made from one region of color to another region of color, and the maximum MG(f) describes the shortest transition distance between the two regions having different hue, saturation, and/or value.

While the MG(f) has, up to this point, been described in terms of a change in magnitude over a pixel, it is necessary to convert this to physical dimensions to account for the resolution of the graphic. This is done according to the following formula:

$$MG(f; mm) = \frac{MG(f; \text{pixel})}{\text{pixel\_size [mm]}}$$

where MG(f;pixel) is as described previously (color gradient magnitude in normalized attribute units per pixel), the pixel size in millimeters/pixel, and MG(f;mm) is the color gradient magnitude in normalized units per millimeter.

Conversely, the maximum magnitude of color gradient can be used to calculate a characteristic edge width in accord with FIG. 16. The inverse of MG yields the length over which a full-scale transition (0-1) is made. The maximum MG quantity then corresponds to the narrowest characteristic width of the transition, and may be calculated for hue, saturation, and value.

EXAMPLE 1

Figure 5:
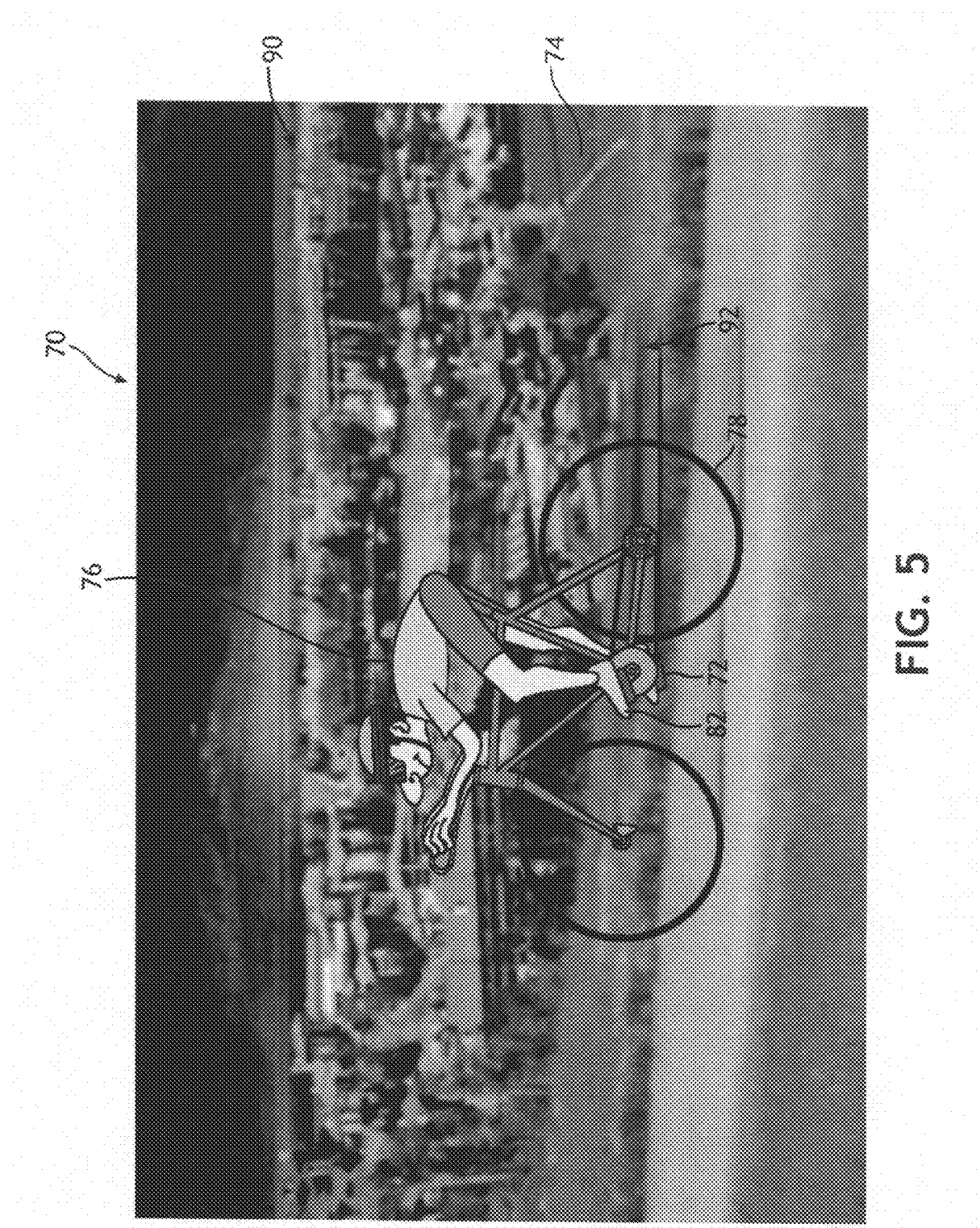
FIG. 5 representatively illustrates a multicolored scene graphic in accordance with one embodiment of the present invention.
Figure 6:
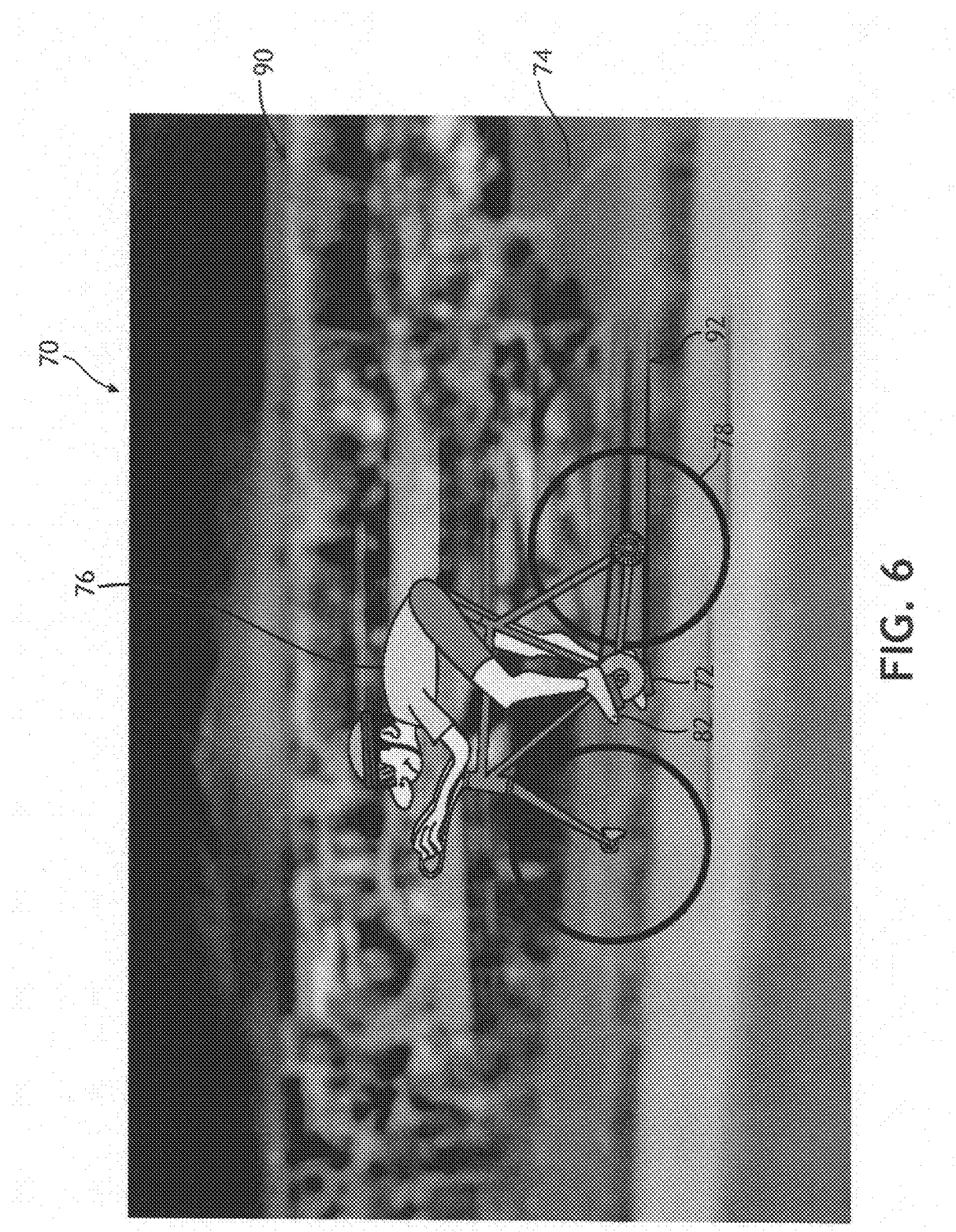
FIG. 6 representatively illustrates a multicolored scene graphic in accordance with another embodiment of the present invention.
Figure 7:
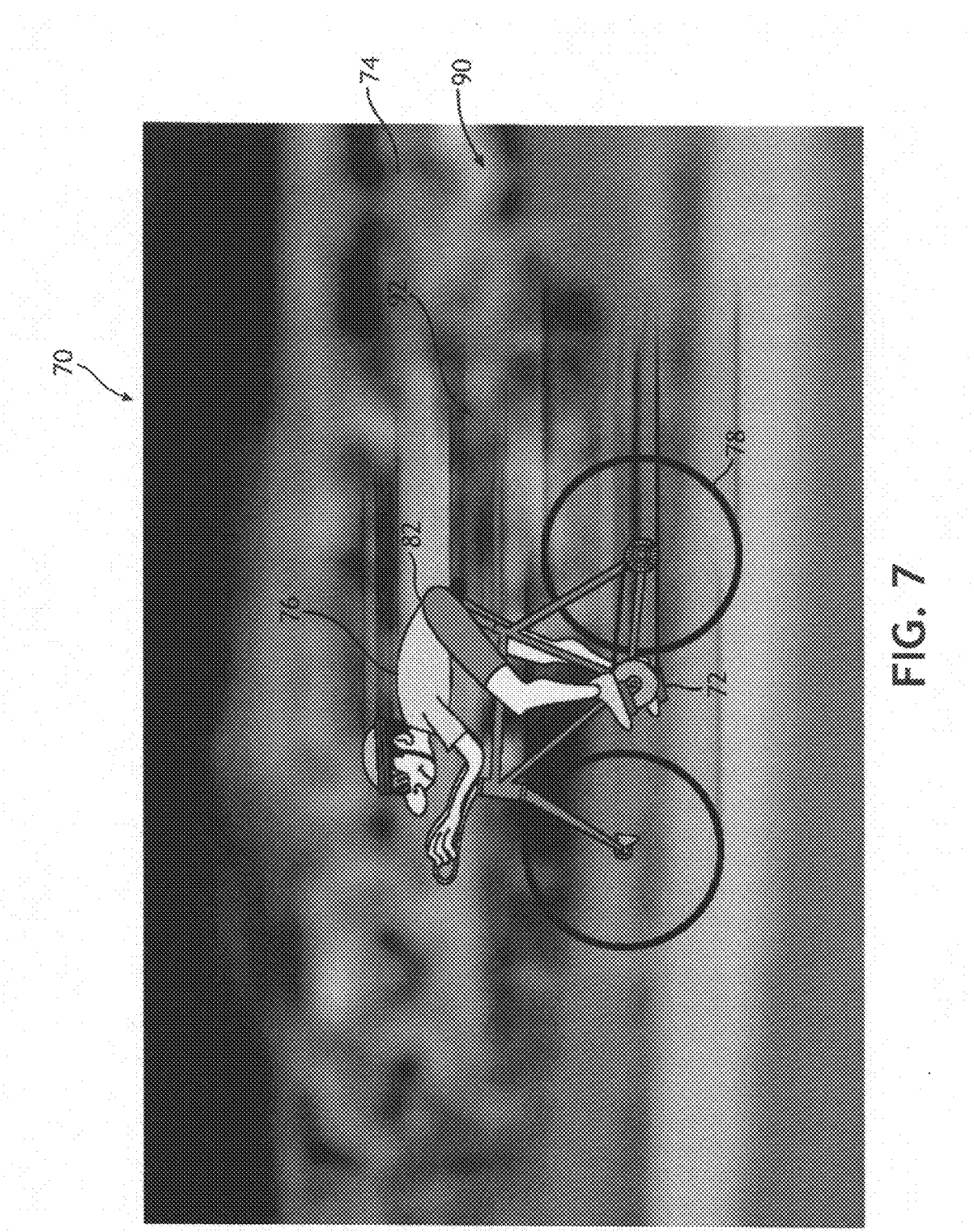
FIG. 7 representatively illustrates a multicolored scene graphic in accordance with yet another embodiment of the present invention.
Figure 8:
FIG. 8 representatively illustrates a background graphic having blurred portions.
Figure 9:
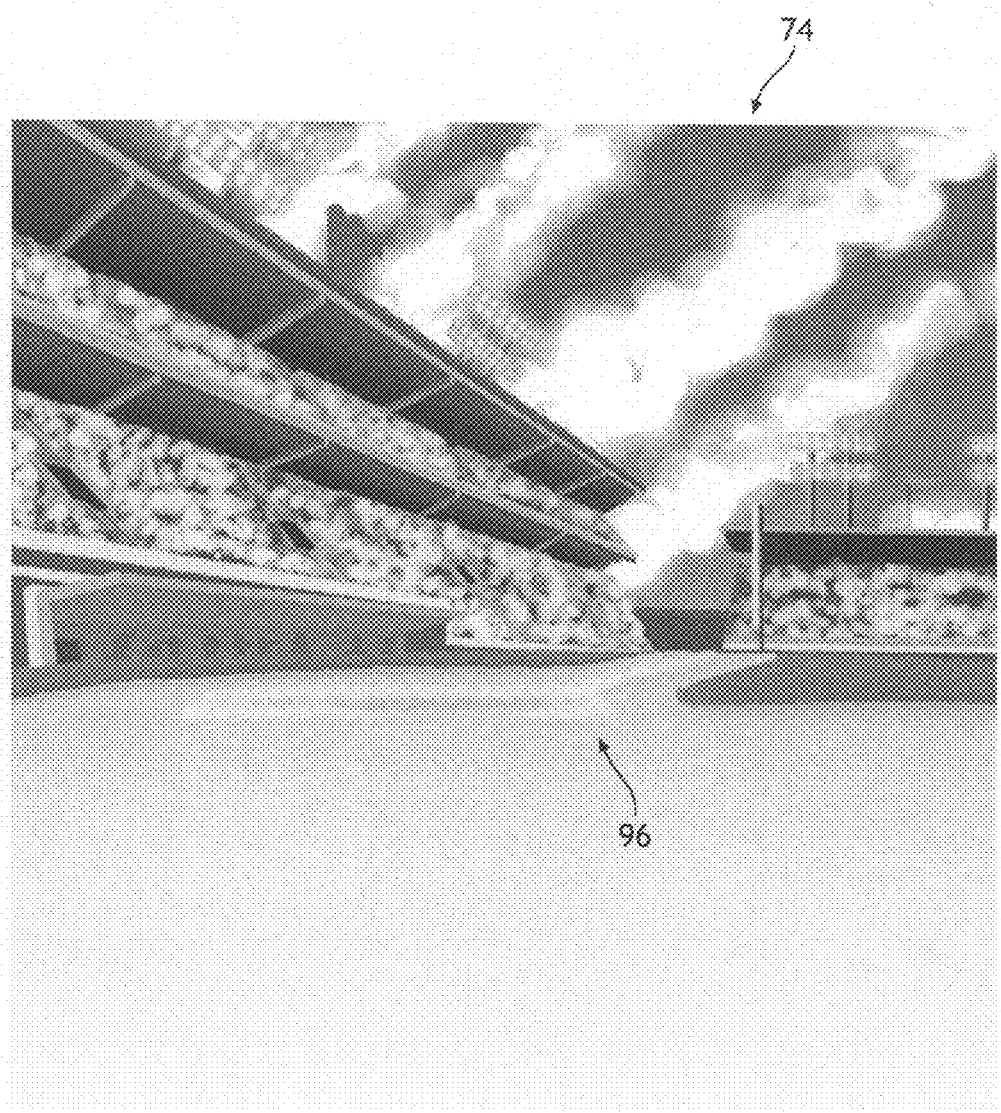
FIG. 9 representatively illustrates a background graphic having blurred portions and exhibiting a cutback effect in accordance with yet another embodiment of the present invention.
Figure 10:
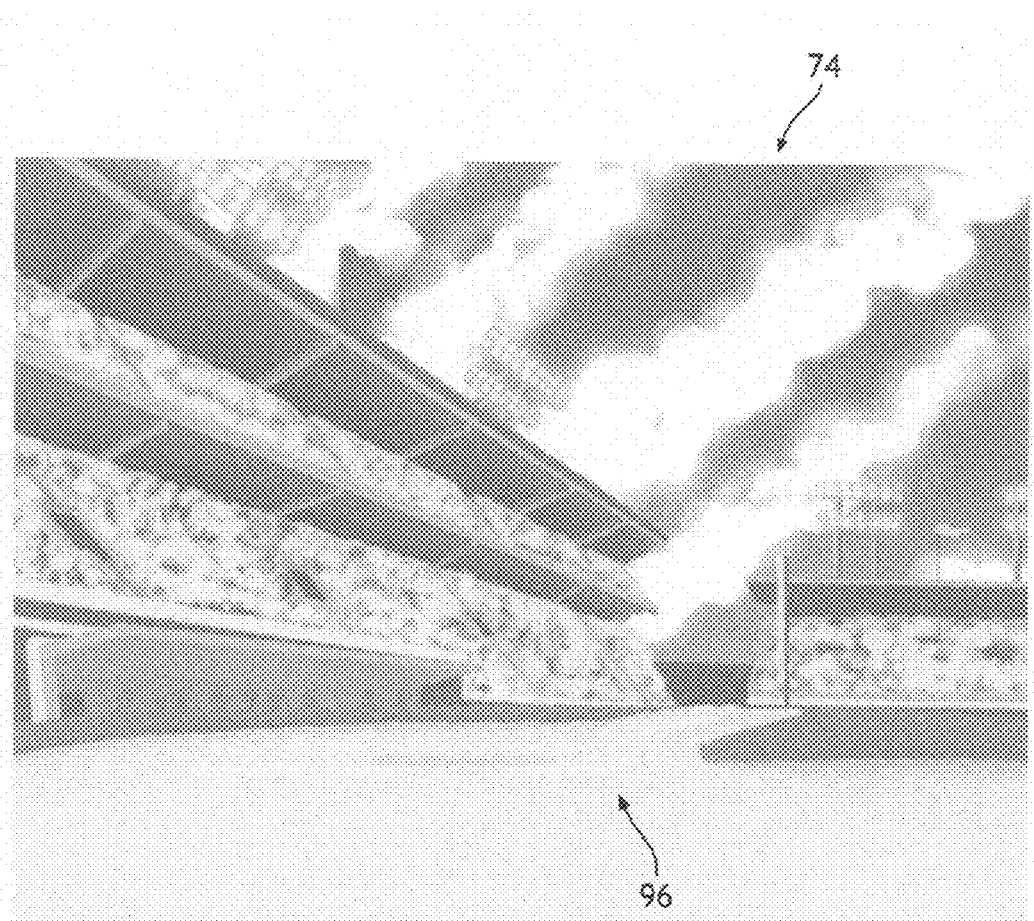
FIG. 10 representatively illustrates a background graphic having blurred portions and exhibiting a cutback effect in accordance with still another embodiment of the present invention.
Figure 11:
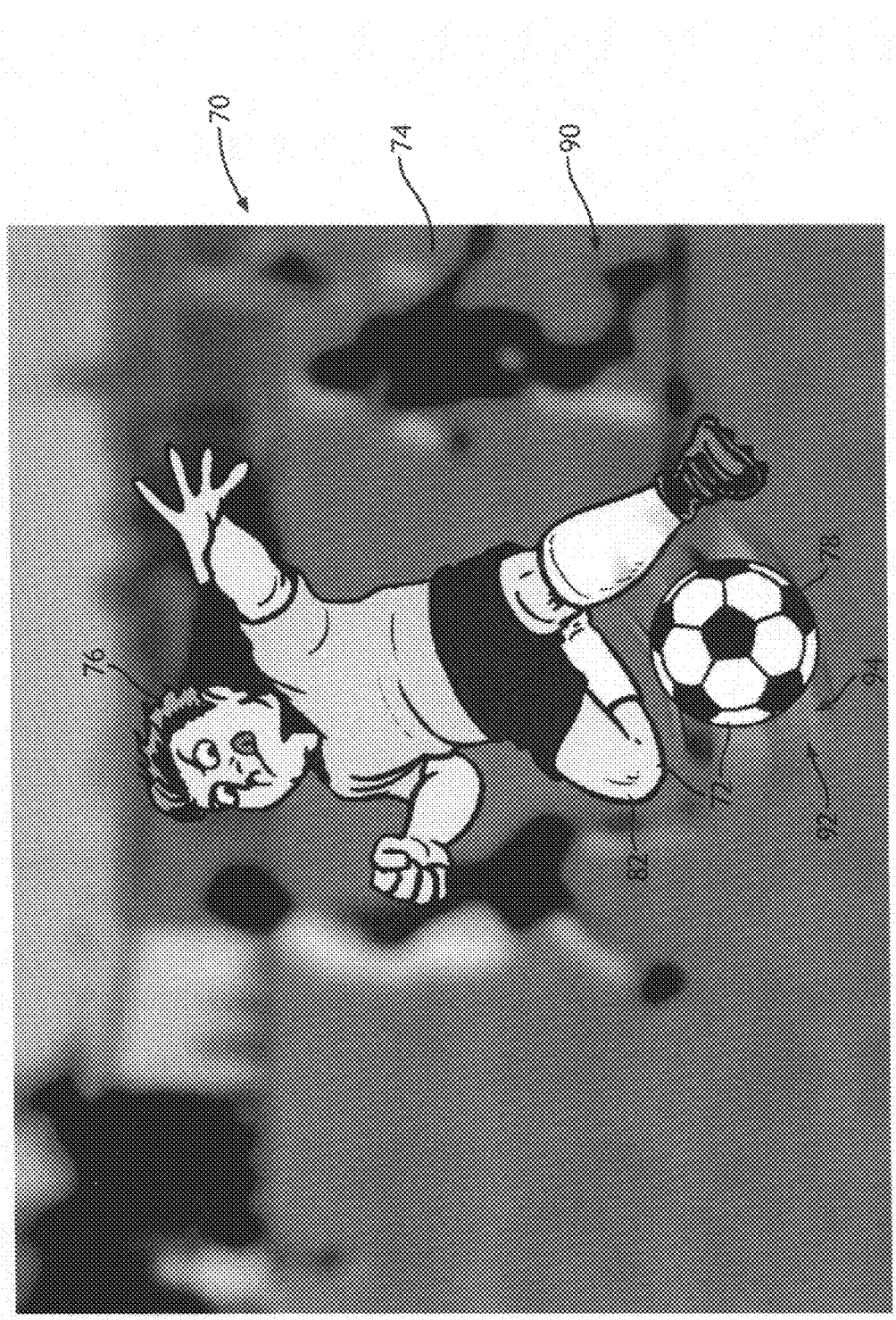
FIG. 11 representatively illustrates a multicolored scene graphic in accordance with another embodiment of the present invention.
Figure 12:
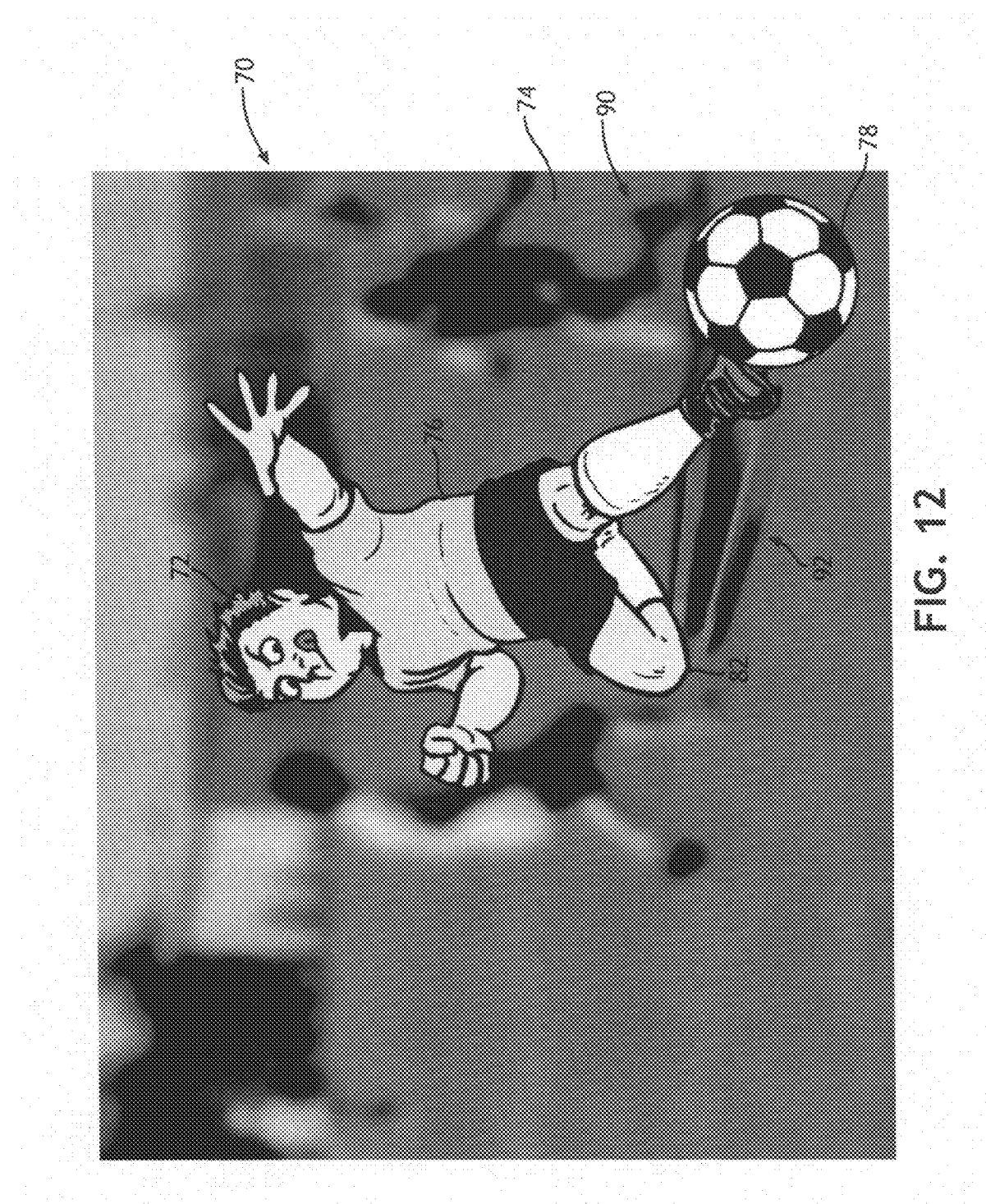
FIG. 12 representatively illustrates a multicolored scene graphic in accordance with still another embodiment of the present invention.
Figure 13:
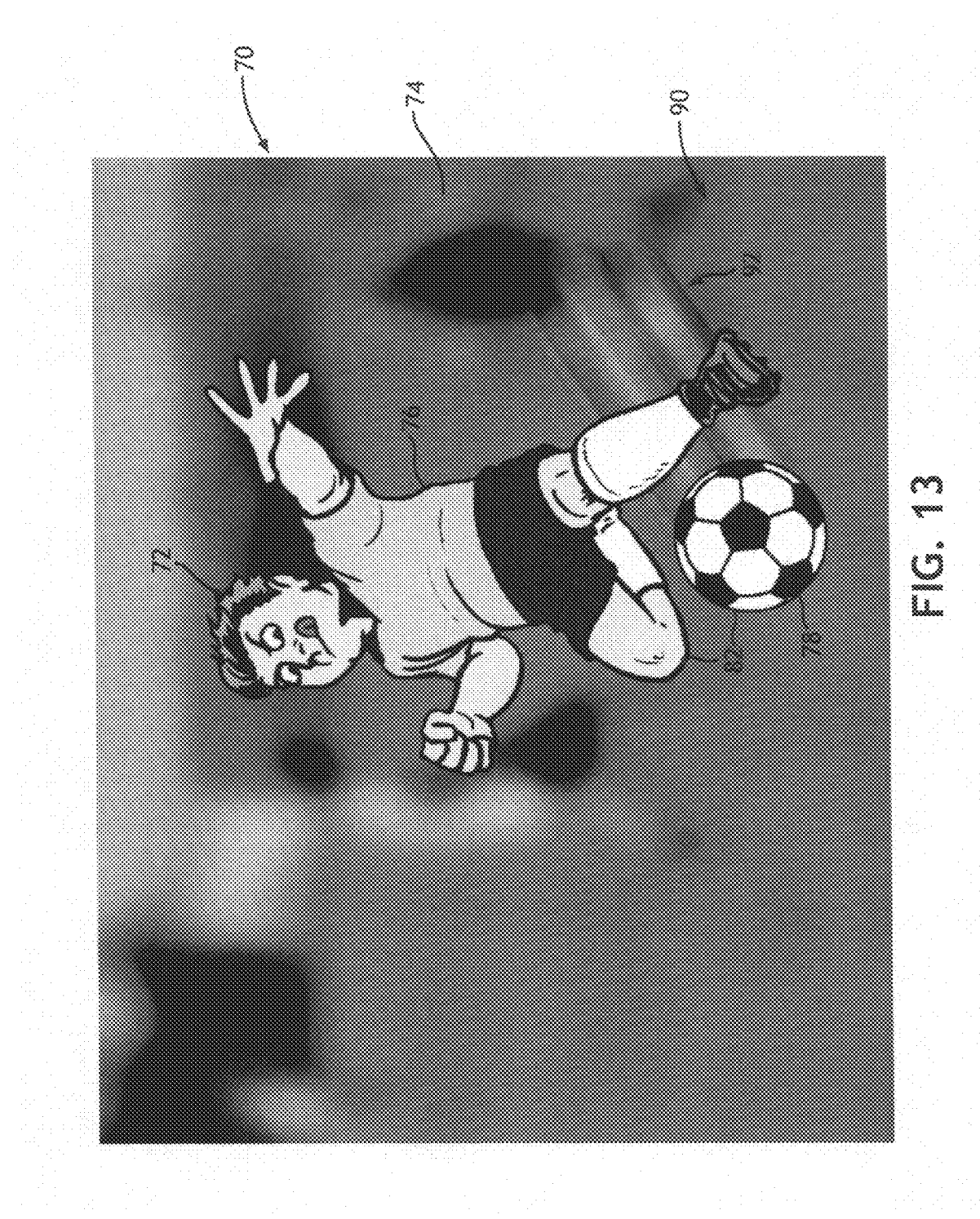
FIG. 13 representatively illustrates a multicolored scene graphic in accordance with yet another embodiment of the present invention.
Figure 14:
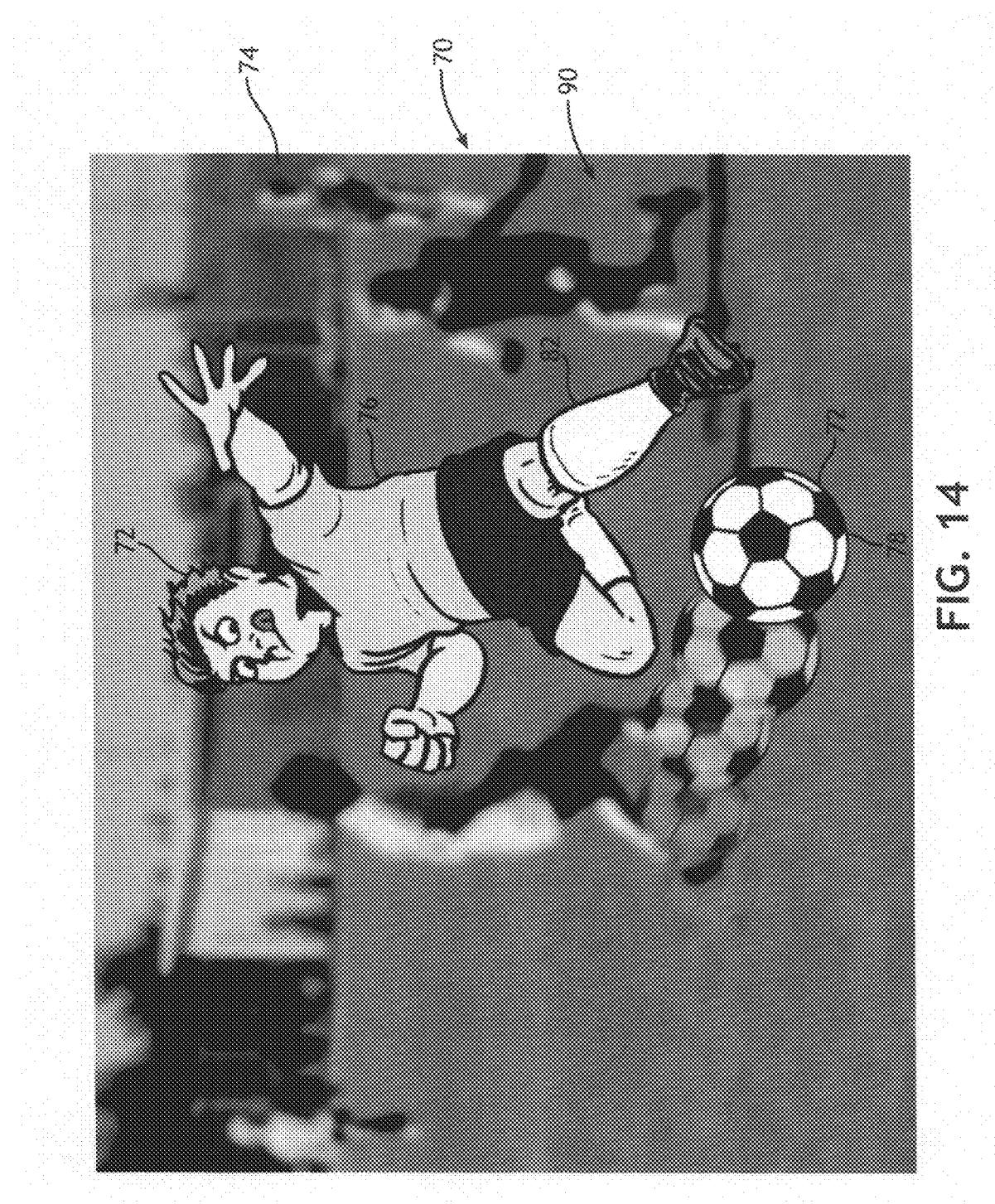
FIG. 14 representatively illustrates a multicolored scene graphic in accordance with still another embodiment of the present invention.

In Example 1, portions of the image shown in FIG. 5 were examined for blur-related attributes. Both a focal graphic ROI and background graphic ROI were chosen containing color transition regions. The focal graphic ROI is taken from the biker's waist area, and the background graphic ROI is taken from the upper right region of the background landscape. The color transitions within the regions of interest were examined using the method described above. The table in FIG. 17 shows the maximum magnitude of the color gradient for each attribute, and the corresponding characteristic widths are shown. In this example, the hue and value characteristic widths of the blurred graphic region are larger than the hue and value characteristic widths of the focal graphic region, implying a larger perceived blur. The saturation characteristic widths of the focal and blurred graphic regions are not significantly different from each other.

EXAMPLE 2

In Example 2, portions of the images shown in FIGS. 18-22 were examined for blur-related attributes. The focal graphic 72 (i.e., the giraffe) is identical in each of FIGS. 18-22, but the background graphic 74 (i.e., the trees and meadow) becomes successively blurrier as one progresses from FIG. 18 to FIG. 22. For each Figure, both a focal graphic ROI and a background graphic ROI were chosen containing color transitions. The focal graphic ROI is taken from the main body of the giraffe of FIG. 22, and the background graphic ROI is taken from the portion of the meadow that includes a tree for each of FIGS. 18-22. The color transitions within the regions of interest were examined using the method described above.

The maximum gradients for hue, saturation, and value were calculated for each ROI using the method described above. The table in FIG. 23 displays each region of interest, as well as the average characteristic widths for hue, saturation and value for the color transitions within each of those regions are shown. In this example, the characteristic widths of each color attribute for the region of interest of the unblurred background graphic are comparable to the characteristic widths of each color attribute for the region of interest of the unblurred focal graphic. However, the characteristic widths of each color attribute for the region of interest of each blurred background graphic are greater than the characteristic widths of each color attribute for the region of interest of the unblurred focal graphic (increasingly so as one progresses from FIG. 19 to FIG. 22), implying a larger perceived blur.

It is notable that as the background graphic increases in blur as one progress from FIG. 18 to FIG. 22, the characteristic widths of each of the three color components—hue, saturation, and value—likewise increase. Therefore, the colorimetric gradients (and thus the perceived blur) can be reasonably expressed as a functionality of the differences, such as the Euclidean norm as indicated above. Thus, the table of FIG. 23 also presents the width of the Euclidean norm of the hue, saturation, and value gradients (the "HSV Width").

Accordingly, the average HSV Width of the background graphic regions of interest can be seen to increase with increasing blur. (Note that the HSV Width is not the norm of the individual hue, saturation, and value widths themselves, but rather is the norm of the individual gradients. Thus, the HSV Width will always be shorter than any one of the hue, saturation, or value widths from which it is derived.)

What is claimed is:

1. A method of producing an absorbent garment having a multicolored scene graphic disposed on a substrate, comprising:
   providing a background graphic design;
   applying a Gaussian blur of at least about 4 pixels to at least about 50% of an area of the background graphic design to create a blurred background graphic design;
   providing a focal graphic design; and
   disposing the blurred background graphic design and the focal graphic design on the substrate.

2. The method of claim 1, wherein the Gaussian blur is applied using digital image software.

3. The method of claim 1, wherein the Gaussian blur is at least about 5 pixels and is applied to at least about 90% of an area of the background graphic design to create the blurred background graphic design.

* * * * *